US012453588B2

(12) United States Patent
Stevens et al.

(10) Patent No.: US 12,453,588 B2
(45) Date of Patent: Oct. 28, 2025

(54) SPIRAL GROWTH TETHER SYSTEMS AND METHODS

(71) Applicants: Peter M. Stevens, Salt Lake City, UT (US); John Colin Stevens, Salt Lake City, UT (US)

(72) Inventors: Peter M. Stevens, Salt Lake City, UT (US); John Colin Stevens, Salt Lake City, UT (US)

( * ) Notice: Subject to any disclaimer, the term of this patent is extended or adjusted under 35 U.S.C. 154(b) by 0 days.

(21) Appl. No.: 19/076,870

(22) Filed: Mar. 11, 2025

(65) Prior Publication Data

US 2025/0281211 A1 Sep. 11, 2025

Related U.S. Application Data

(60) Provisional application No. 63/676,412, filed on Jul. 28, 2024, provisional application No. 63/563,848, filed on Mar. 11, 2024.

(51) Int. Cl.
*A61B 17/80* (2006.01)
*A61B 17/84* (2006.01)
(Continued)

(52) U.S. Cl.
CPC ............ *A61B 17/842* (2013.01); *A61B 90/39* (2016.02); *A61B 2017/681* (2013.01); *A61B 2090/3966* (2016.02)

(58) Field of Classification Search
CPC .................. A61B 17/842; A61B 90/39; A61B 2090/3966; A61B 2017/681
(Continued)

(56) References Cited

U.S. PATENT DOCUMENTS 5,269,784 A * 12/1993 Mast ...................... A61B 17/60 606/288
5,951,557 A 9/1999 Luter
(Continued)

FOREIGN PATENT DOCUMENTS

| | | | |
|---|---|---|---|
| CN | 216221622 | U | 4/2022 |
| WO | 2020107072 | A1 | 6/2020 |
| WO | 2024201429 | A1 | 10/2024 |

OTHER PUBLICATIONS

Orthopediatrics, GIRO Growth Modulation System, as early as Jan. 24, 2024. https://www.orthopediatrics.com/products/giro-growth-modulation-system-pega-orthopediatrics/.
(Continued)

*Primary Examiner* — Eduardo C Robert
*Assistant Examiner* — David C Comstock
(74) *Attorney, Agent, or Firm* — David Meibos; Maywood IP Law

(57) ABSTRACT

A spiral growth tether system may be securable to a bone having a growth plate that separates a first portion of the bone from a second portion of the bone. The spiral growth tether system may include a tether including a first end configured to be secured to the first portion, a second end configured to be secured to the second portion, and a central portion between the first end and the second end. The first end and the second end may be configured to separate at the central portion in response to the first end being urged away from the second end as a result of growth of the bone urging the first portion away from the second portion.

20 Claims, 30 Drawing Sheets

(51) Int. Cl.
*A61B 90/00* (2016.01)
*A61B 17/68* (2006.01)

(58) Field of Classification Search
USPC ..... 606/60, 280, 70, 71, 281, 283, 284, 285, 606/286, 290, 298, 328, 105, 90
See application file for complete search history.

(56) References Cited

U.S. PATENT DOCUMENTS

| | | | | |
|---|---|---|---|---|
| 6,017,345 | A * | 1/2000 | Richelsoph | A61B 17/7059 606/291 |
| 6,423,061 | B1 | 7/2002 | Bryant | |
| 7,077,844 | B2 * | 7/2006 | Michelson | A61B 17/1604 606/279 |
| 7,306,601 | B2 | 12/2007 | McGrath | |
| RE40,914 | E | 9/2009 | Taylor | |
| 7,811,312 | B2 | 10/2010 | Stevens et al. | |
| 8,029,507 | B2 | 10/2011 | Green | |
| 8,055,487 | B2 | 11/2011 | James | |
| 8,133,230 | B2 | 3/2012 | Stevens et al. | |
| 8,273,111 | B2 | 9/2012 | Amato et al. | |
| 8,425,520 | B2 | 4/2013 | Zalenski | |
| 8,574,232 | B1 | 11/2013 | Ross et al. | |
| 8,641,742 | B2 | 2/2014 | Stevens et al. | |
| 8,801,760 | B2 | 8/2014 | Amato et al. | |
| 9,066,756 | B2 | 6/2015 | Wong | |
| 9,439,696 | B2 | 9/2016 | Pierce | |
| 9,579,134 | B2 | 2/2017 | Amato et al. | |
| 9,770,272 | B2 | 9/2017 | Thoren et al. | |
| 9,808,289 | B2 | 11/2017 | Ross et al. | |
| 9,877,755 | B2 | 1/2018 | Sampath et al. | |
| 10,080,585 | B2 | 9/2018 | Singh et al. | |
| 10,130,401 | B2 | 11/2018 | Amato et al. | |
| 10,149,701 | B2 | 12/2018 | Crozet et al. | |
| 10,603,076 | B2 | 3/2020 | Ross et al. | |
| 10,660,672 | B2 | 5/2020 | Siemer et al. | |
| 10,682,161 | B2 | 6/2020 | Magni et al. | |
| 10,842,509 | B2 | 11/2020 | Little | |
| 11,006,987 | B2 | 5/2021 | Venturini et al. | |
| 11,457,965 | B1 * | 10/2022 | Evans | A61B 17/8625 |
| 11,701,154 | B2 | 7/2023 | Venturini et al. | |
| 2002/0128655 | A1 * | 9/2002 | Michelson | A61B 17/8052 606/70 |
| 2004/0111089 | A1 | 6/2004 | Stevens et al. | |
| 2005/0119656 | A1 | 6/2005 | Ferrante et al. | |
| 2006/0142767 | A1 | 6/2006 | Green | |
| 2007/0093834 | A1 * | 4/2007 | Stevens | A61B 17/8085 606/279 |
| 2007/0162019 | A1 | 7/2007 | Burns et al. | |
| 2007/0270851 | A1 * | 11/2007 | Erickson | A61B 17/8042 623/17.16 |
| 2008/0051685 | A1 | 2/2008 | Benenati et al. | |
| 2008/0161816 | A1 | 7/2008 | Stevens et al. | |
| 2008/0306550 | A1 | 12/2008 | Matityahu | |
| 2009/0198235 | A1 | 8/2009 | Steiner et al. | |
| 2010/0137916 | A1 * | 6/2010 | Hynes | A61B 17/7059 606/301 |
| 2011/0106169 | A1 | 5/2011 | Zalenski | |
| 2012/0016427 | A1 | 1/2012 | Stindel | |
| 2012/0078251 | A1 | 3/2012 | Benenati et al. | |
| 2012/0191139 | A1 | 7/2012 | Stevens et al. | |
| 2012/0209338 | A1 | 8/2012 | Groiso | |
| 2012/0271358 | A1 | 10/2012 | Stevens et al. | |
| 2012/0323287 | A1 | 12/2012 | Pierce | |
| 2013/0165980 | A1 * | 6/2013 | Cook | A61B 17/8047 606/286 |
| 2015/0032166 | A1 | 1/2015 | Amato et al. | |
| 2015/0196398 | A1 * | 7/2015 | Camprasse | A61L 27/3604 606/301 |
| 2015/0216565 | A1 | 8/2015 | Paley et al. | |
| 2015/0257803 | A1 | 9/2015 | Sampath | |
| 2015/0313652 | A1 * | 11/2015 | Burckhardt | A61B 90/94 606/71 |
| 2016/0022176 | A1 * | 1/2016 | Le Huec | A61B 6/461 600/594 |
| 2018/0021050 | A1 | 1/2018 | Little | |
| 2018/0221058 | A1 | 8/2018 | Bilger et al. | |
| 2019/0254711 | A1 | 8/2019 | Mullaney et al. | |
| 2020/0038079 | A1 | 2/2020 | Windolf | |
| 2020/0107860 | A1 | 4/2020 | Stevens | |
| 2020/0323569 | A1 | 10/2020 | Venturini | |
| 2020/0397480 | A1 | 12/2020 | Lavoritano | |

OTHER PUBLICATIONS

Amari et al., “Guiding Femoral Rotational Growth in an Animal Model”, J Bone Joint Surg Am. 2013;95:2022-2027.
Cobanoglu et al., “Rotational deformities of the long bones can be corrected with rotationally guided growth during the growth phase: A study in rabbits”, Acta Orthopaedica 2016; 87 (3): 301-305.
Metaizeau et al., “New femoral derotation technique based on guided growth in children”, Orthopaedics & Traumatology: Surgery & Research 105 (2019) 1175-1179.
Lazarus et al, “Torsional Growth Modulation of Long Bones by Oblique Plating in a Rabbit Model”, J. Pediatr Orthop 2018;38(2):e97-e103.
International Search Report and Written Opinion dated May 7, 2025 for corresponding International Application No. PCT/US2025/019445.

* cited by examiner

250

Start Angle (degrees) / Treatment Time (months)

| Plate Length | 20 mm | | 26 mm | | 32 mm | |
|---|---|---|---|---|---|---|
| Femur Width /Correction | 54 mm | 59 mm | 60 mm | 66 mm | 67 mm | 72 mm |
| 10 degrees | 60 / 3 | 59 / 3 | 63 / 3 | 61 / 3 | 64 / 3 | 63 / 3 |
| 15 degrees | 52 / 5 | 50 / 5 | 56 / 5 | 54 / 5 | 58 / 5 | 56 / 6 |
| 20 degrees | 43 / 7 | 40 / 9 | 49 / 7 | 46 / 9 | 52 / 8 | 49 / 9 |
| 25 degrees | -- | -- | 41 / 11 | 36 / 13 | 45 / 11 | 42 / 13 |
| 30 degrees | -- | -- | -- | -- | 37 / 16 | 33 / 18 |

FIG. 6

SPIRAL GROWTH TETHER SYSTEMS AND METHODS

CROSS REFERENCE TO RELATED APPLICATIONS

The present application claims the benefit of U.S. Provisional Application No. 63/563,848 filed on Mar. 11, 2024, entitled "ROTATIONAL GUIDED GROWTH TETHERS, SYSTEMS, AND METHODS", and U.S. Provisional Application No. 63/676,412 filed on Jul. 28, 2024, entitled "ROTATIONAL GUIDED GROWTH TETHERS, SYSTEMS, AND METHODS". The foregoing documents are hereby incorporated by reference in their entirety.

TECHNICAL FIELD

The present disclosure relates to bone fixation devices, systems, and methods. More specifically, the present disclosure relates to spiral growth tethers assemblies, systems, and methods for surgically changing the rotational alignment of intact bones.

BACKGROUND

Rotational deformities of the bones of the lower extremities can change the relative alignment of the hip, knee, and ankle, resulting in acute or chronic joint pathology. During adolescence, malrotation predisposes to hip and knee injuries. During adulthood, the cumulative effects may culminate in degenerative arthritis of the hip and/or knee. In the transverse plane, inclination of the femoral neck in the upper femur with respect to the transcondylar axis of the lower femur is referred to as femoral version (FIG. 1A). In normal human development, femoral version is approximately 11°. This results in the knee, ankle and foot pointed in a forward direction (FIG. 1C).

The term anteversion refers to excessive inward torque of the femur as depicted in FIG. 1D (total of 41°=30° excessive torsion). This causes obligate in-toeing (FIG. 1E). This is not a benign situation because it may predispose to hip problems (torn labrum) and/or knee problems (patellar instability or torn ligamentous structures) consequent to acute or repetitive trauma. Less frequently, outward femoral torsion (retroversion) is manifest by the knee rotating outward, relative to the hip.

Normal tibial alignment allows for up to 15° of outward rotation of the ankle/foot, relative to the knee. In contradistinction, outward tibial torsion is defined as the amount of excessive torsion beyond that range (FIG. 2A). Normal alignment is again depicted from behind (FIG. 2B) and top-down, with the foot neutral (FIG. 2C). Outward tibial torsion, beyond 15°, is another example of long bone malrotation. Viewing the legs from behind, outward tibial torsion is depicted in FIG. 2D. Top-down views of a normal tibia vs. outward torsion, each superimposed over the bones of a foot, is depicted in FIG. 2F. Outward torsion may cause biomechanical problems in the knee, ankle, and foot.

Persistent rotational deformity cannot be corrected with a brace or with physical therapy, leaving surgical treatment as the only recourse. The traditional procedure for correcting malrotation of the femur or tibia comprises osteotomy (cutting the bone). The degree of rotational correction is typically in the 20° to 30° range. A long plate and screws or an intramedullary rod may then be implanted to hold the transected bone portions in a corrected rotational alignment, pending healing. This inpatient surgery is extremely invasive and may have adverse sequelae. Negative side effects may include: (1) significant pain associated with bone cutting and healing; (2) relatively large incision and resulting large scar with increased blood loss and risk of surgical site infection and wound complications, (3) risk of loss of bone fixation or implant failure and subsequent reoperation; (4) risk of delayed bone healing or non-union (5) risk of neurovascular injury, etc. Weightbearing and activities are restricted until the bone has healed. The implants are usually removed once the bone has healed, requiring a secondary procedure.

Accordingly, improved implant devices, systems, and methods that can avert some, or all, of these negative side effects would be desirable, by avoiding osteotomy altogether.

SUMMARY

The various systems and methods of the present disclosure have been developed in response to the present state of the art, and in particular, in response to the problems and needs in the art that have not yet been fully solved by currently available spiral growth tether systems and methods.

In some embodiments, a spiral growth tether system may be securable to a bone having a growth plate that separates a first portion of the bone from a second portion of the bone. The spiral growth tether system may include a tether including a first end configured to be secured to the first portion, a second end configured to be secured to the second portion, and a central portion between the first end and the second end. The first end and the second end may be configured to separate at the central portion in response to the first end being urged away from the second end as a result of growth of the bone urging the first portion away from the second portion.

In the spiral growth tether system of any preceding paragraph, the central portion may include a frangible region comprising a groove configured to reduce a cross-sectional area of the frangible region such that, in response to the first end being urged away from the second end, the frangible region may break at the groove.

In the spiral growth tether system of any preceding paragraph, the central portion may include a frangible region comprising one or more apertures extending thorough the frangible region, thereby reducing a cross-sectional area of the frangible region such that in response to the first end being urged away from the second end, the frangible region may break at the one or more apertures.

In the spiral growth tether system of any preceding paragraph, the tether may include a strap formed of a polymer.

In the spiral growth tether system of any preceding paragraph, the spiral growth tether system may further include comprising a first coupling member configured to secure the first end to the first portion and a second coupling member configured to secure the second end to the second portion. The first end and the second end may be configured to apply a rotational force to the first portion relative to the second portion in response to the first end being urged away from the second end as a result of growth of the bone urging the first portion away from the second portion, with the first end secured to the first portion and the second end secured to the second portion, the first coupling member may be configured to allow the first end to rotate relative to the first portion and the second coupling member may be configured to allow the second end to rotate relative to the second portion, and, with the first end secured to the first portion, the second end secured to the second portion, and the first end separated from the second end, the spiral growth tether system may be configured to permit growth of the bone.

In the spiral growth tether system of any preceding paragraph, the first end may include a first plurality of radiopaque beads, the second end may include a second plurality of radiopaque beads, and the first plurality of radiopaque beads and the second plurality of radiopaque beads may be configured as markers for radiostereometric analysis of the growth plate.

In the spiral growth tether system of any preceding paragraph, wherein the first plurality of radiopaque beads may include three radiopaque beads configured in a first triangular pattern, and the second plurality of radiopaque beads may include three radiopaque beads configured in a second triangular pattern.

In some embodiments, a spiral growth tether system may be securable to a bone having a growth plate that separates a first portion of the bone from a second portion of the bone. The spiral growth tether system may include a first coupling member having a first head portion and a first shoulder portion configured to seat against a first surface on the first portion of the bone, a second coupling member having a second head portion and a second shoulder portion configured to seat against a second surface on the second portion of the bone, and a tether including a first end having a first aperture configured to receive the first coupling member, a second end having a second aperture configured to receive the second coupling member, and a central portion between the first end and the second end. The first end may be configured to be secured to the first portion of the bone via the first coupling member so that the first shoulder portion may be seated against the first surface of the bone and the first head portion may be spaced apart from the first end, the second end may be configured to be secured to the second portion of the bone via the second coupling member so that the second shoulder portion may be seated against the second surface of the bone and the second head portion may be spaced apart from the second end, and, with the first end secured to the first portion and the second end secured to the second portion, the first coupling member may be configured to allow the first end to rotate relative to the first portion and the second coupling member may be configured to allow the second end to rotate relative to the second portion.

In the spiral growth tether system of any preceding paragraph, the first end and the second end may be configured to separate at the central portion in response to the first end being urged away from the second end as a result of growth of the bone urging the first portion away from the second portion.

In the spiral growth tether system of any preceding paragraph, the central portion may include a frangible region having a groove configured to reduce a cross-sectional area of the frangible region such that, in response to the first end being urged away from the second end, the frangible region may break at the groove.

In the spiral growth tether system of any preceding paragraph, the central portion may include a frangible region having one or more apertures extending thorough the frangible region, thereby reducing a cross-sectional area of the frangible region such that in response to the first end being urged away from the second end, the frangible region may break at the one or more apertures.

In the spiral growth tether system of any preceding paragraph, the first end and the second end may be configured to apply a rotational force to the first portion relative to the second portion in response to the first end being urged away from the second end as a result of growth of the bone urging the first portion away from the second portion, and, with the first end secured to the first portion, the second end secured to the second portion, and the first end separated from the second end, the spiral growth tether system may be configured to permit growth of the bone.

In the spiral growth tether system of any preceding paragraph, the first end may include a first plurality of radiopaque beads, the second end may include a second plurality of radiopaque beads, and the first plurality of radiopaque beads and the second plurality of radiopaque beads may be configured as markers for radiostereometric analysis of the growth plate.

In the spiral growth tether system of any preceding paragraph, the first plurality of radiopaque beads may include three radiopaque beads configured in a first triangular pattern, and the second plurality of radiopaque beads may include three radiopaque beads configured in a second triangular pattern.

In some embodiments, a spiral growth tether system may be securable to a bone having a growth plate that separates a first portion of the bone from a second portion of the bone. The spiral growth tether system may include a tether including a first end configured to be secured to the first portion, and a second end configured to be secured to the second portion. The tether may include a strap formed of a polymer, and the first end and the second end may be configured to separate in response to the first end being urged away from the second end as a result of growth of the bone urging the first portion away from the second portion.

In the spiral growth tether system of any preceding paragraph, the tether may further include a central portion between the first end and the second end, wherein the central portion may include a frangible region having a groove configured to reduce a cross-sectional area of the frangible region such that, in response to the first end being urged away from the second end, the frangible region may break at the groove.

In the spiral growth tether system of any preceding paragraph, the tether may further include a central portion between the first end and the second end, wherein the central portion may include a frangible region having one or more apertures extending thorough the frangible region, thereby reducing a cross-sectional area of the frangible region such that in response to the first end being urged away from the second end, the frangible region may break at the one or more apertures.

In the spiral growth tether system of any preceding paragraph, the first end may include a first plurality of radiopaque beads, the second end may include a second plurality of radiopaque beads, and the first plurality of radiopaque beads and the second plurality of radiopaque beads may be configured as markers for radiostereometric analysis of the growth plate.

In the spiral growth tether system of any preceding paragraph, the spiral growth tether system may further include a first coupling member having a first shoulder portion, the first coupling member configured to secure the first end to the first portion, and a second coupling member having a second shoulder portion, the second coupling member configured to secure the second end to the second portion. With the first coupling member secured to the first portion, the first shoulder portion may be configured to seat against a first surface of the bone, with the second coupling member secured to the second portion, the second shoulder portion may be configured to seat against a second surface of the bone, and with the first end secured to the first portion and the second end secured to the second portion, the first coupling member may be configured to allow the first end to rotate relative to the first portion and the second coupling member may be configured to allow the second end to rotate relative to the second portion.

In the spiral growth tether system of any preceding paragraph, with the first end secured to the first portion, the second end secured to the second portion, and the first end separated from the second end, the spiral growth tether system may be configured to permit growth of the bone.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 6 is a table showing a relationship between correction angle, femur width, start angle, and treatment time for plate lengths of 20 mm, 26 mm and 32 mm, respectively.

Figure 1A:
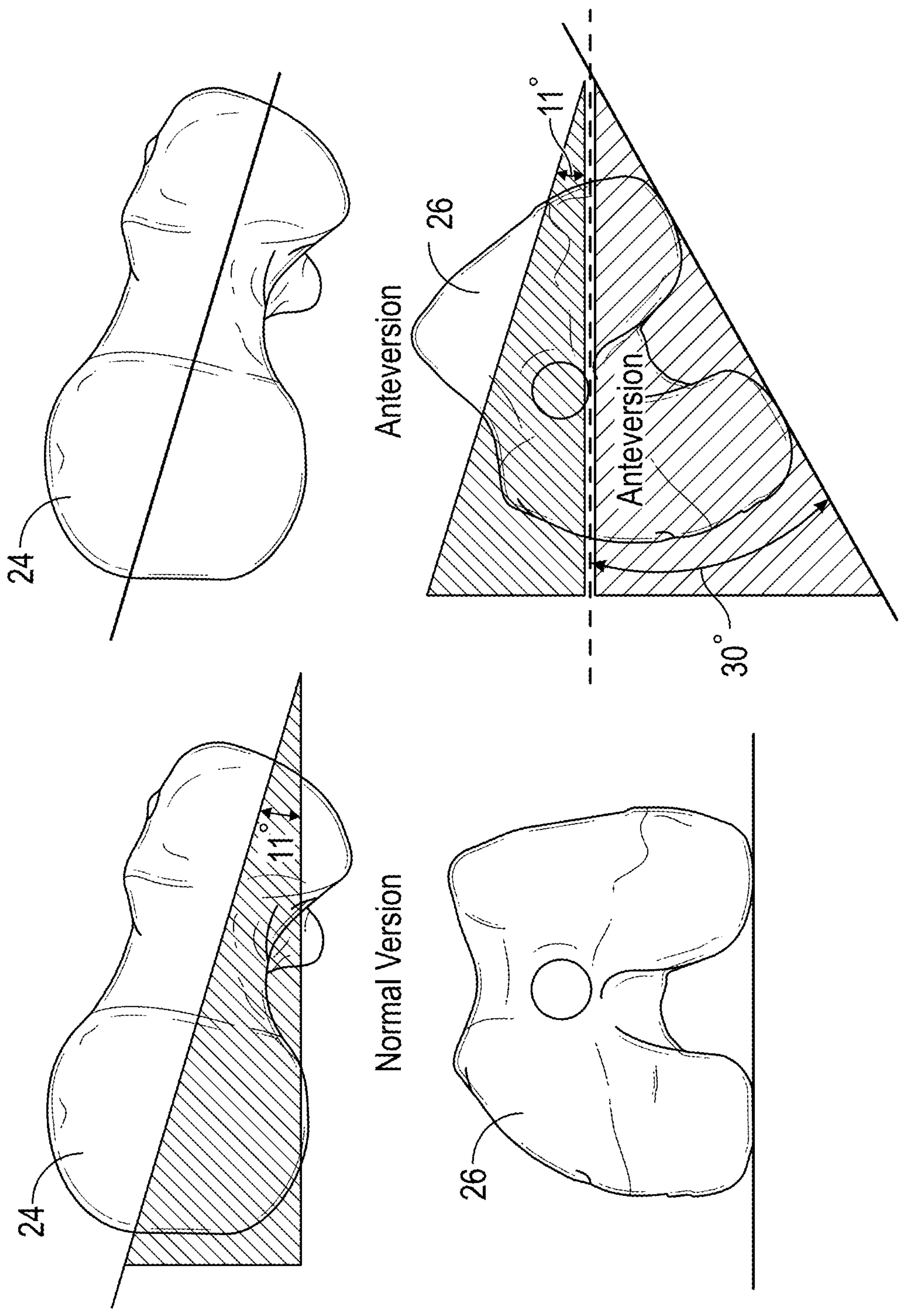
FIG. 1A is a top-down view showing the proximal and distal femur. When superimposed, the head-neck axis is superimposed upon the transcondylar axis, subtending a normal femoral version angle of 11°. Femoral anteversion is measured by an increase in this angle (shown here as measuring) 30°.

It is to be understood that the drawings are for purposes of illustrating the concepts of the present disclosure and may be drawn to scale, or may include variations from scale drawings. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

It will be understood that any feature of any embodiment described or contemplated herein may be combined with any other embodiment that is described or contemplated herein without departing from the spirit or scope of the present disclosure.

The present disclosure is related to U.S. Pat. No. 7,811,312, filed on Dec. 4, 2002 and entitled "BONE ALIGNMENT IMPLANT AND METHOD OF USE", which is incorporated by reference as though set forth herein in its entirety. The present disclosure is also related to U.S. Pat. No. 8,133,230, filed on Mar. 19, 2008 and entitled "BONE ALIGNMENT IMPLANT AND METHOD OF USE", which is incorporated by reference as though set forth herein in its entirety.

Figure 1C:
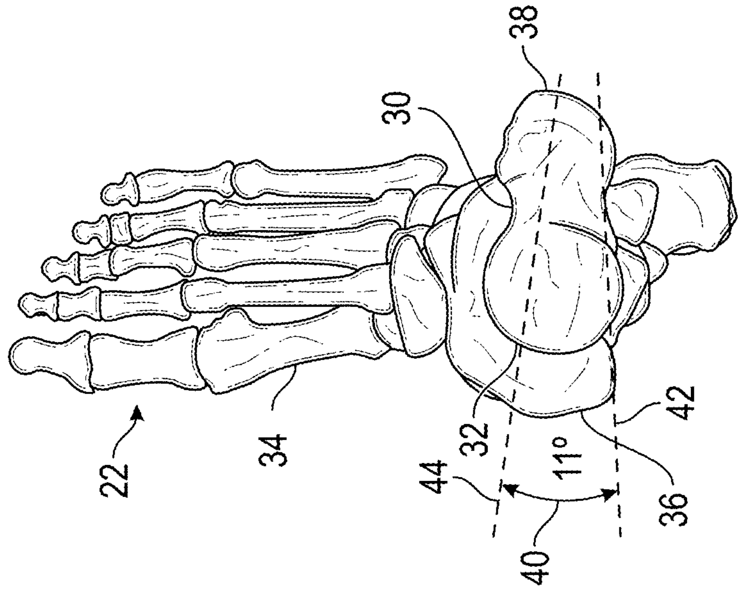
FIG. 1C is a top-down view of the right lower extremity of FIG. 1B, with the foot facing forward.
Figure 1B:
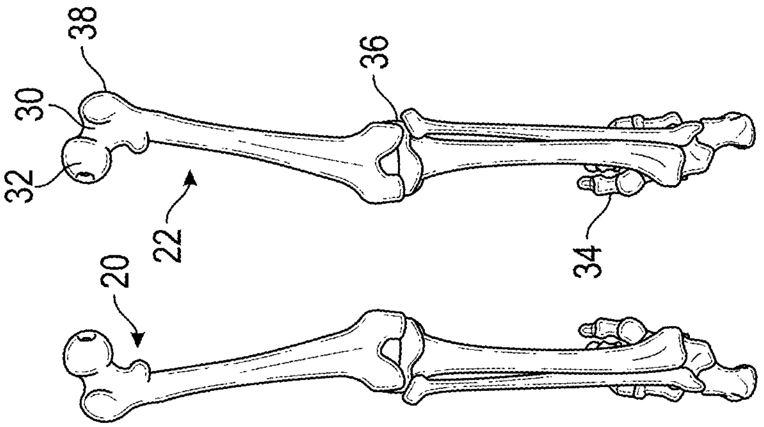
FIG. 1B is a posterior view of lower skeletal extremities with normal femoral version (11°).

FIG. 1A is a top-down view showing the proximal femur 24 and distal femur 26. When superimposed, the head-neck axis is superimposed upon the transcondylar axis, subtending a normal femoral version angle of 11°. Femoral anteversion is measured by an increase in this angle (shown here as measuring) 30°. FIG. 1B is a posterior view (i.e.: a view from a posterior viewpoint) of the lower skeletal extremities showing normal alignment of the left extremity 20 and the right extremity 22 in the pediatric population. FIG. 1C is a top-down view of the right extremity 22, showing the normal 11° version of the femoral neck 30 and femoral head 32, relative to the distal femur 26. It can be appreciated in FIG. 1C that the foot 34 is well aligned with the knee 36 and the hip 38. Version is the angle 40, measured between a line 42 tangent to the posterior condyles of the distal femur, also referred to herein as the transcondylar axis, and a line 44 that bisects the femoral neck and head. In FIG. 1B, the angle 40 is 11°, which is normal by adolescence.

Figure 1E:
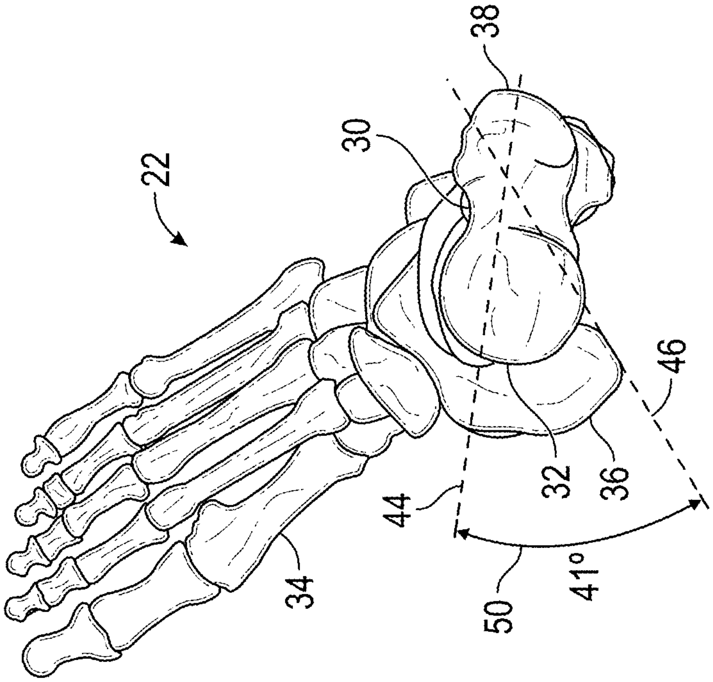
FIG. 1E is a top-down view of the right lower extremity of FIG. 1D. The femoral anteversion causes the knee and foot to point inward. This is manifest by in-toeing gait.
Figure 1D:
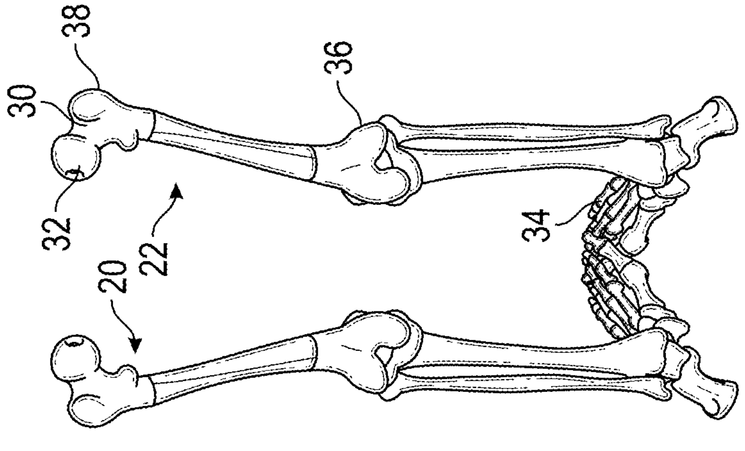
FIG. 1D is a posterior view of lower skeletal extremities with femoral anteversion.

FIG. 1D is a posterior view of the left extremity 20 and the right extremity 22 showing an abnormal alignment of the left extremity 20 and the right extremity 22. FIG. 1E is a top-down view of the right extremity 22, showing the anteversion of the femoral neck 30 and femoral head 32. It can be appreciated in FIG. 1E that the foot 34 and the knee 36 are turned inward relative to the hip 38. In FIG. 2B, the anteversion angle 50 is 41° (measured between the line 44 that bisects the femoral neck and head and a line 46 tangent to the posterior condyles of the distal femur), which is outside the normal range in the general population. This abnormal anteversion is observed as "in-toeing" of the feet, causing the left foot to be over rotated in the clockwise direction and the right foot 34 to be over rotated in the counterclockwise direction, as viewed when looking down at the feet from a standing position. Abnormal anteversion is also referred to as a rotational or torsional deformity, represented by an angle measured in the transverse plane. It can cause "in-toeing" as mentioned above, or less commonly splay the foot outward (femoral retroversion). Either can beneficially be corrected via the present disclosure. Although anteversion is used as a specific example, those of skill in the art will recognize that the techniques, implants, and principles taught by this disclosure may be applied to other rotational deformities in femurs and/or tibia.

FIG. 1D provides an example of a bilateral femoral rotational deformity, which is common when femoral rotational deformity is present; however, unilateral femoral rotational deformities are also occasionally present in the pediatric population. Although the preceding discussion is limited to the femur, it is understood that rotational defects can exist in other bones of the extremities, such as the tibia, and that the devices, systems and methods presented herein are equally applicable to other extremity bones, including but not limited to any other bones of the legs, feet, arms or hands.

Figure 2A:
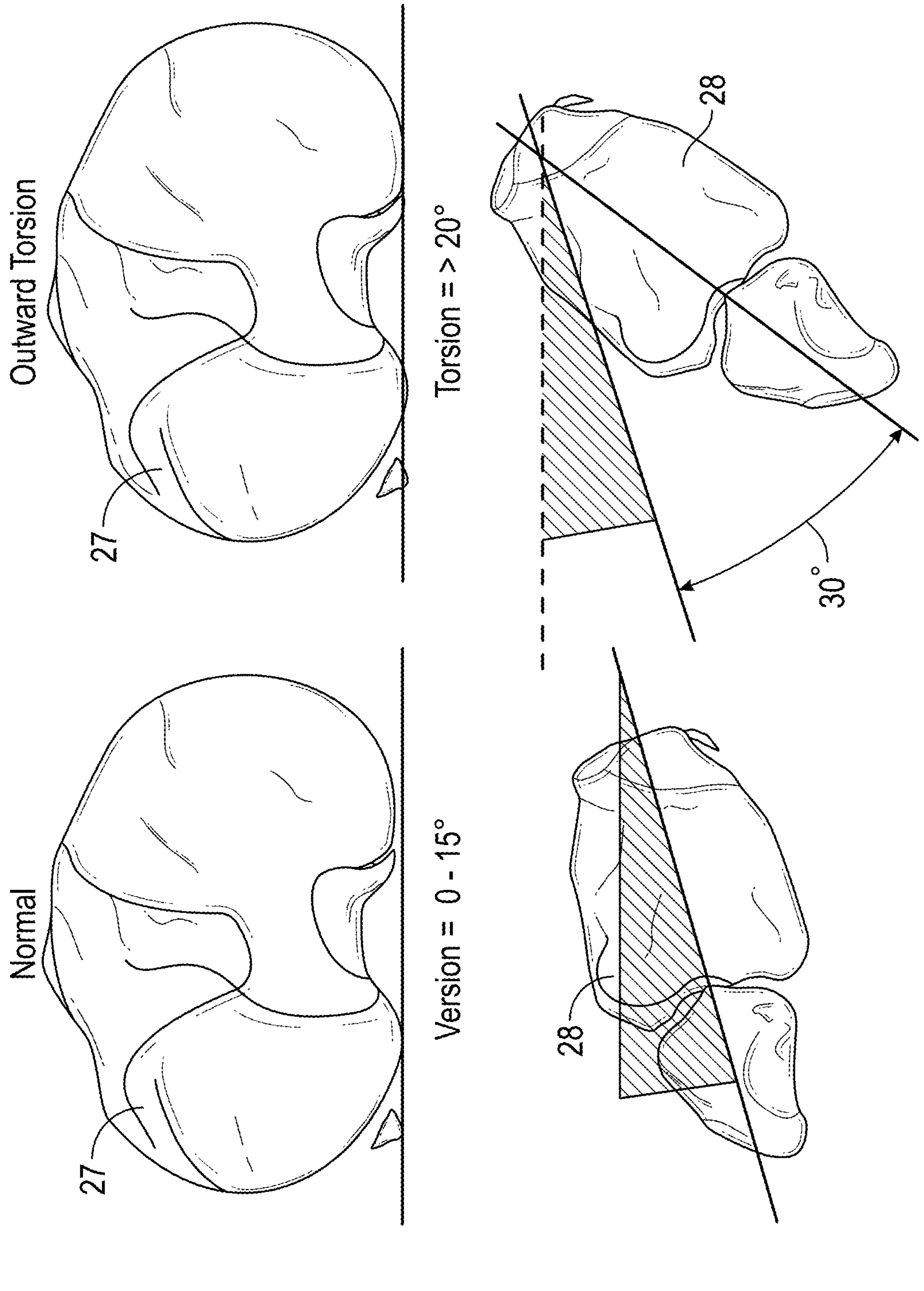
FIG. 2A is a top-down view of the proximal tibia and distal tibia (ankle). When superimposed the axis of the tibial condyles, superimposed upon the ankle, subtends a normal range of 0°-15°. Outward tibial torsion is defined by the torque in excess of that range.
Figure 2C:
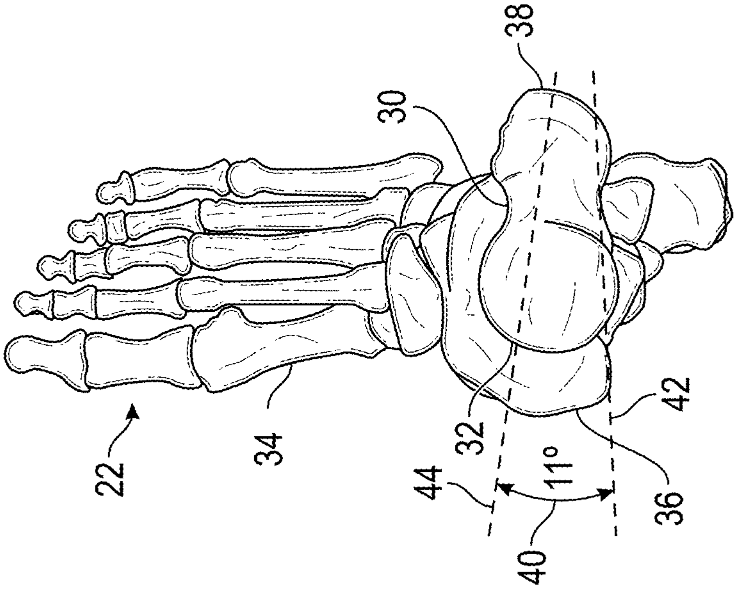
FIG. 2C is a top-down view of the normal tibia of FIG. 2B, with the foot facing forward.
Figure 2B:
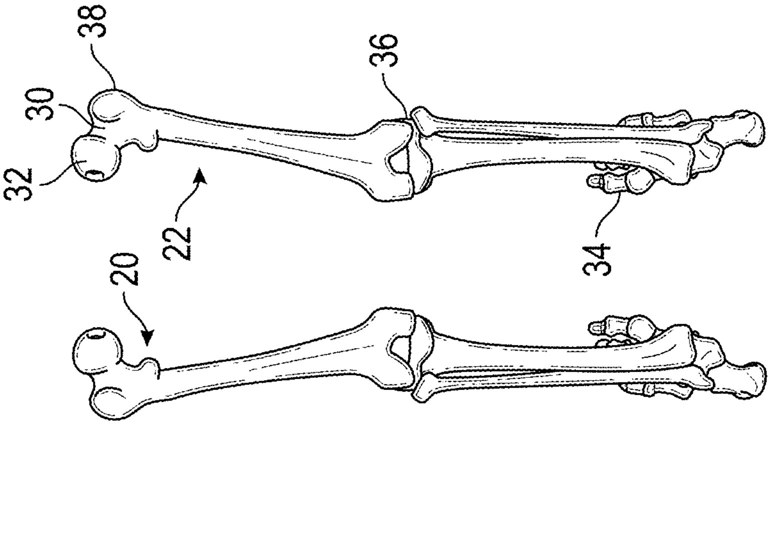
FIG. 2B is a posterior view of lower skeletal extremities with normal tibial version (range 0°-15°).
Figure 2E:
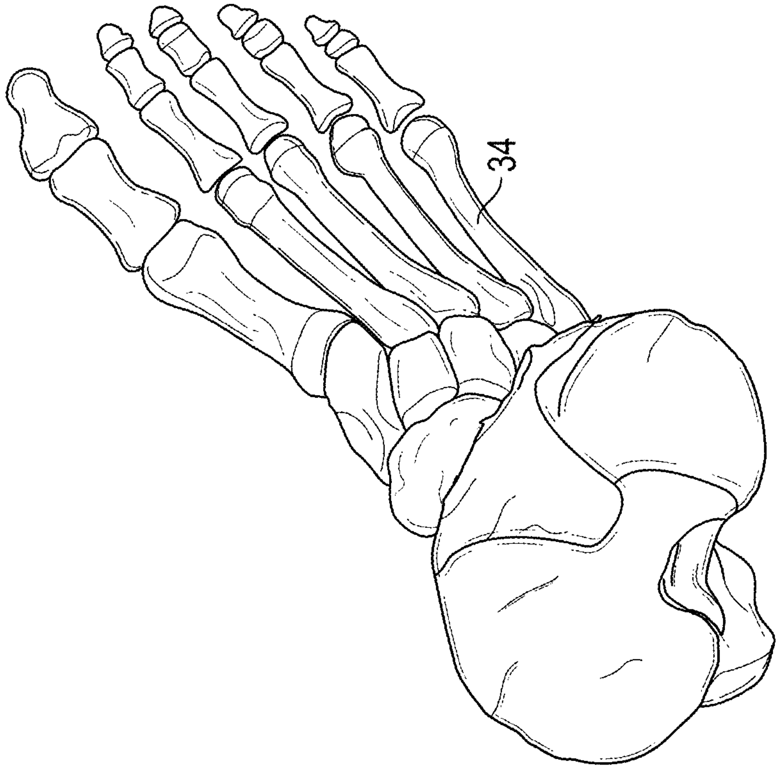
FIG. 2E is a top-down view of the upper tibia of FIG. 2D, with outward torsion, superimposed on the foot that is forced to point outward. This is manifest by out-toeing gait.
Figure 2D:
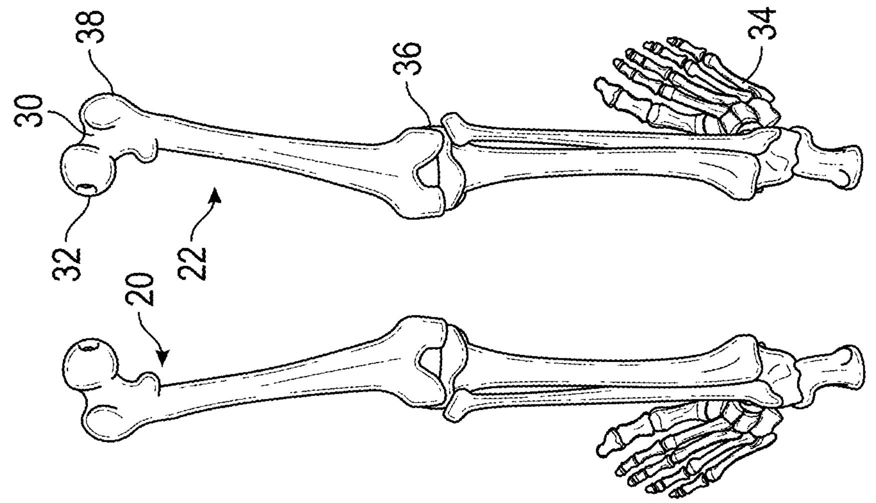
FIG. 2D is a posterior view of the lower extremities with outward tibial torsion.
Figure 2F:
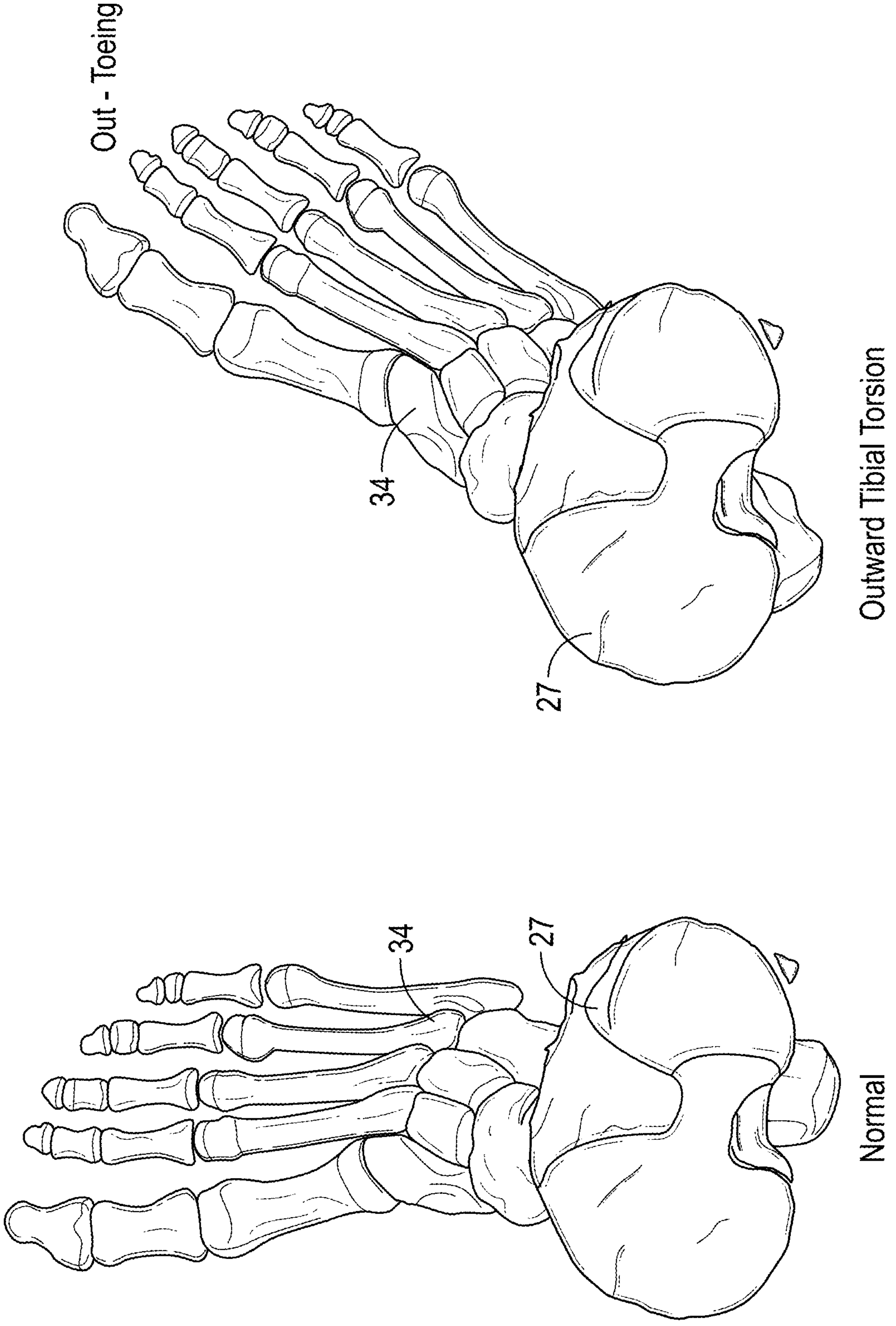
FIG. 2F is a top-down view of normal alignment vs. outward tibial torsion and out-toeing.

FIG. 2A is a top-down view of the proximal tibia 27 and distal tibia 28 (ankle). When superimposed, the axis of the tibial condyles, superimposed upon the ankle, subtends a normal range of 0°-15°. Outward tibial torsion is defined by the torque in excess of that range. FIG. 2B is a posterior view of lower skeletal extremities with normal tibial version (range 0°-15°). FIG. 2C is a top-down view of the normal tibia of FIG. 2B, with the foot facing forward. FIG. 2D is a posterior view of the lower extremities with outward tibial torsion. FIG. 2E is a top-down view of the upper tibia of FIG. 2D, with outward torsion, superimposed on the foot that is forced to point outward. This is manifest by out-toeing gait. FIG. 2F is a top-down view of normal alignment vs. outward tibial torsion and out-toeing.

The most common tibial deformity is outward torsion, which can also cause knee problems. The knee and ankle are essentially hinge joints. When they are not working in the same plane, considerable torsional strain may be imposed upon the knee and ankle. The normal posterior view FIG. 2B and top-down views FIG. 2C are again depicted for comparison. FIG. 2D is the posterior view of the legs in a patient with outward tibial torsion. FIG. 2E is a top-down view of the tibia, superimposed on the ankle and foot with obligate out-toeing. Comparison of normal alignment vs. outward tibial torsion is again depicted in FIG. 2F.

In more extreme cases of pan-genu torsion, patients have the cumulative effects of femoral anteversion plus outward tibial torsion. In these unfortunate individuals, while the foot is pointed forward, the knee is pointing inward by as much as 60° or more, relative to the hip and ankle. Heretofore, the only surgical remedy for these patients includes four staged osteotomies.

The spiral growth tether systems and methods presented herein are equally applicable to other extremity bones in the feet, arms and/or hands.

Figure 3B:
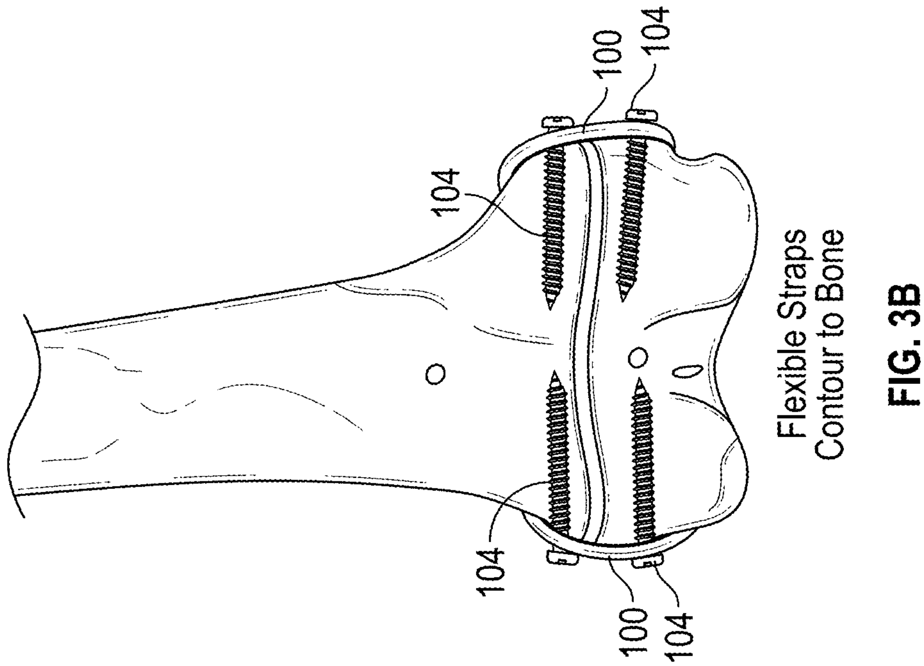
FIG. 3B is a frontal view of the distal femur, with self-contouring oblique tethers applied to the medial and lateral femur. Being broad and flexible, they may not damage the periosteum that protects the growth plate and surrounds the bone, as spiral growth ensues.
Figure 3A:
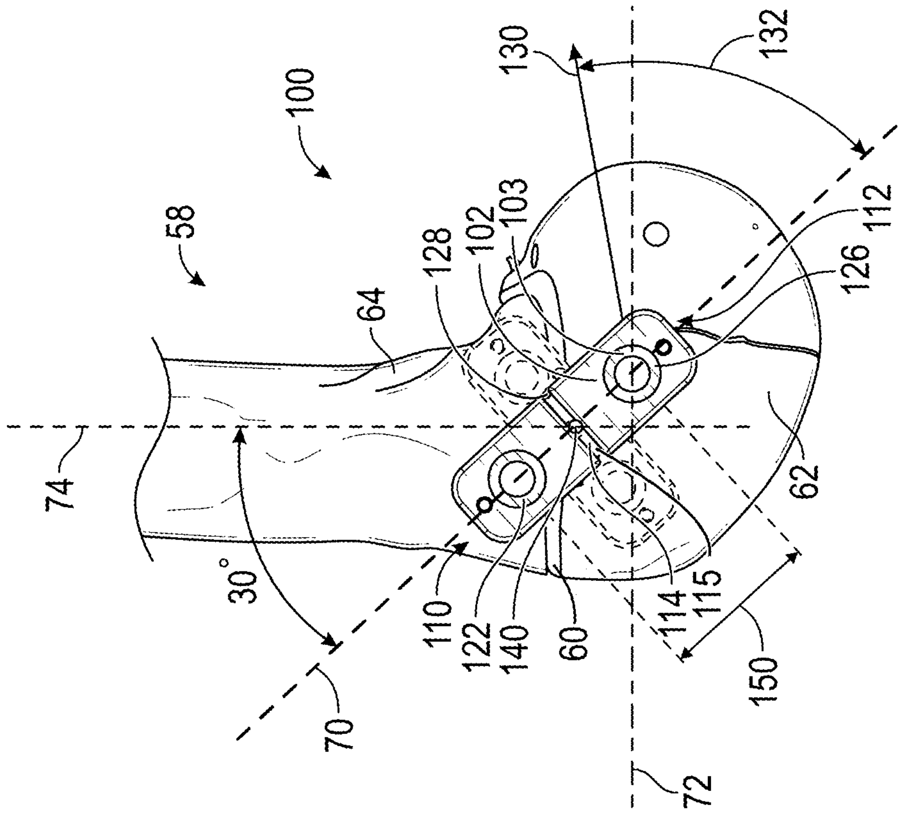
FIG. 3A is a medial view of a right pediatric femur with a tether assembly according to one embodiment attached, spanning the growth plate. The tether is mounted at an oblique angle, relative to the shaft, that matches the desired rotational correction (typically 20°-30°). A corresponding tether is shown placed laterally, mirroring the angle.

FIG. 3A is a medial view of the distal portion of a right femur 58 showing a physis 60, also referred to as a growth plate, and showing an embodiment of the present invention. The growing femur 58 has an epiphyseal portion 62 distal to the physis 60, and a metaphyseal portion 64 proximal to the physis 60. The physis 60, comprised of cartilage, is situated between the epiphyseal portion 62 from the metaphyseal portion 64. The femur 58 may be a pediatric femur, which may continue to grow longitudinally from the physis 60, until skeletal maturity is reached (approximately 14 years in girls and 16 years in boys).

FIG. 3B is a frontal view of the distal femur of FIG. 3A, with self-contouring oblique tethers applied to the medial and lateral femur. Being broad and flexible, they may not damage the periosteum that protects the growth plate and surrounds the bone, as spiral growth ensues.

Figure 3C:
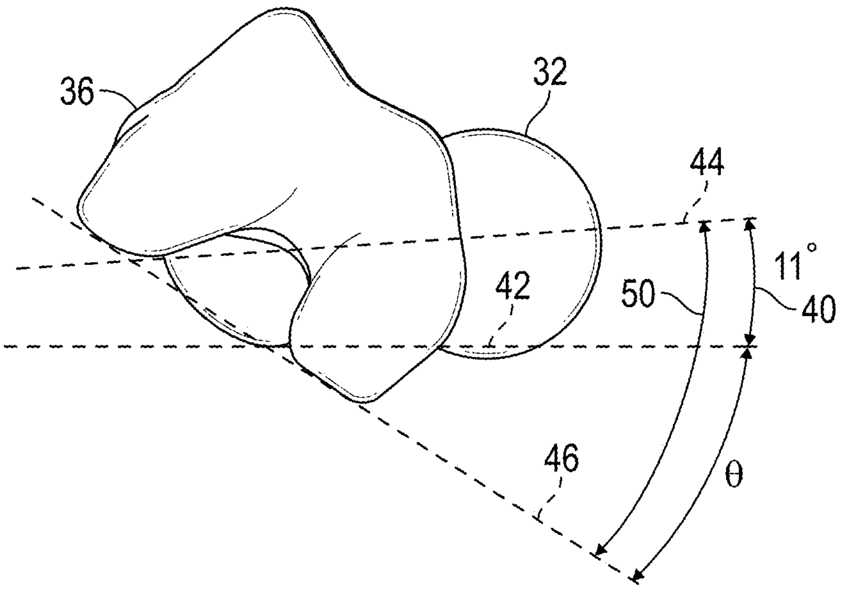
FIG. 3C is a bottom-up view of the femur of FIG. 3A, demonstrating 11° of version+30° of anteversion (41° total).

FIG. 3C is a bottom-up view of the femur of FIG. 3A, demonstrating 11° of version+30° of anteversion (41° total). It can be appreciated in FIG. 2F that the femur 58 has abnormal anteversion; the degree of abnormality is shown as the angle θ in FIG. 3C. This angle θ is the amount of anteversion in excess of the normal anteversion angle of 11°. The angle θ may be the anteversion angle 50 of FIG. 3C minus the anteversion angle 40 (11°) of FIG. 1C. It is desirable to correct the rotational deformity by rotating the distal end of the femur 58 by 0° relative to the proximal end of the femur 58, so that the posterior condyles of the femur 58 are restored to a normal alignment with the femoral neck and head of the femur 58. To ensure that the induced rotational change in the femur 58 is radially symmetric, a second tether assembly may advantageously be placed obliquely on a second side of the femur 58. In the case of the distal end of the femur 58, the second tether assembly may be placed on the lateral side of the femur 58, opposite and radially symmetrical to the placement of the tether assembly 100 on the medial side as shown in FIGS. 3A and 3B.

Coupled to the distal portion of the femur 58 is a tether assembly 100, which may include a tether 102, also referred to herein as a "bone tether," two grommets 103, and two coupling members 104, which are also referred to herein as "bone screws." The tether 102 may have a first end 110, a second end 112, and a central portion 114 extending between the first end 110 and the second end 112. The first end may include a first aperture 122 configured to receive one of the grommets 103. The second end may include a second aperture 126 configured to receive one of the grommets 103.

The tether 102 may be fabricated from any of a variety of biocompatible materials, such as but not limited to: ultra-high molecular weight polyethylene (UHMWPE), polyetheretherketone (PEEK), carbon fiber reinforced PEEK, biodegradable polymers such as poly-L-lactic acid (PLLA), other low tensile strength biocompatible material, and combinations of the foregoing. Alternatively, the tether 102 may be a hybrid construct in which the central portion 114 is comprised of a low tensile strength biocompatible material and the first end 110 and the second end 112 are comprised of a rigid material.

Alternatively, the tether 102 may be formed of a composite material using any of the aforementioned polymers. The composite material may be customized to provide high stiffness and strength in the direction of highest tensile stresses, such as along a longitudinal axis of the tether 102, but provide more flexibility and compliance in other directions, to allow the tether 102 to better conform to the contours of the bone surface of the distal portion of the femur 58. In some embodiments, the tether 102 may be resorbable. During the ensuing rotational growth, the flexible tethers may not damage the periosteum around the growth plate (as wire or rigid metal implants might).

The coupling members 104 and the grommets 103 may be fabricated from a biocompatible material including, but not limited to: stainless steel, titanium and its alloys, nickel titanium alloy, polyetheretherketone (PEEK) or any other biocompatible material with sufficient tensile strength to allow threaded engagement of one of the coupling members 104 with a bone. The materials for the coupling members 104 and the grommets 103 may be chosen so that they are electrochemically and mechanically compatible with each other and with the material used for the tether 102. The coupling members 104 may be a modification of a bone screw that may be customary in the orthopedic arts.

Figure 3D:
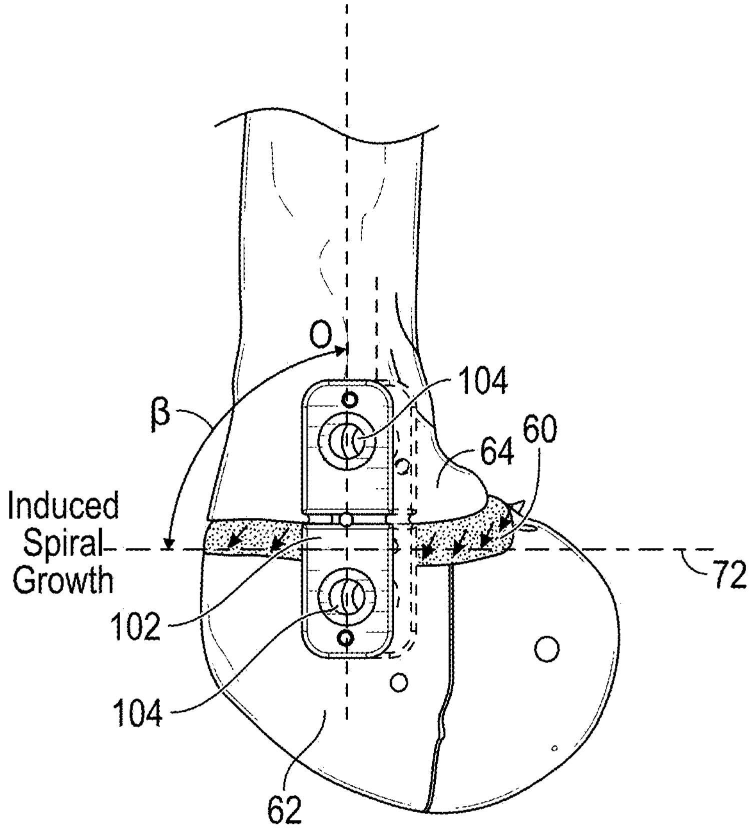
FIG. 3D is a medial view of a right femur with the tether assembly of FIG. 3A, depicting correction of malrotation because tethers have induced spiral growth while assuming a vertical position.

In the prior art, virtually all current bone screws have a convex undersurface on the head that is countersunk into the bone plate to firmly compress the plate against the bone. In contradistinction to this accepted principle, the pan-head screw may have a smooth proximal shank (4 mm) that engages the grommet and expressly avoids compression of the tether against the bone. This arrangement may facilitate swivel of the plate within the grommet so that the tethers reorient vertically with growth, becoming parallel to the long axis of the bone (FIG. 3D).

In alternative embodiments (not shown), coupling members may include staples, suture anchors, pins, tacks and/or other bone fastening devices known to those skilled in the art. Coupling members 104 and grommets 103 may also be made resorbable if desired.

The grommets 103 may be configured to be captively and rotatably received within the first aperture 122 and the second aperture 126. Additionally, each one of the grommets 103 may receive a coupling member 104. The coupling members 104 may be in direct contact with the grommets 103 and the grommets 103 may be in direct contact with a surface of a bone, thereby allowing the tether 102 to freely rotate as the bone grows and the angle $\alpha$ increases. Since the tether 102 may be allowed to freely rotate, the rotation of the tether 102 may not exert a rotational force on the coupling members 104, thereby reducing the risk of disengaging the coupling members 104 from the bone.

The tether assembly 100 shown in FIG. 3A and FIG. 3B may be coupled to the medial side of the distal portion of the femur 58. The first end 110 and the second end 112 of the tether 102 may each be secured to the femur 58 by one of the coupling members 104 securing one of the grommets 103 to the femur 58.

The central portion 114 of the tether 102 may extend generally perpendicular to a longitudinal axis 70 passing through the first end 110 and the second end 112. The central portion 114 may include a frangible region 115 including a groove 128 configured to reduce a cross-sectional area of the frangible region 115 such that, in response to the first end 110 being urged away from the second end 112, the frangible region 115 may break at the groove 128. An initial angle 132 may exist between the direction 130 and the longitudinal axis 70 of the tether 102. The initial angle 132 may be a constant for all patients, or may be selected on a patient-specific basis to control the desired amount of anteversion correction. The initial angle 132 may match the desired degree of correction (typically 20°-30°).

Figure 3E:
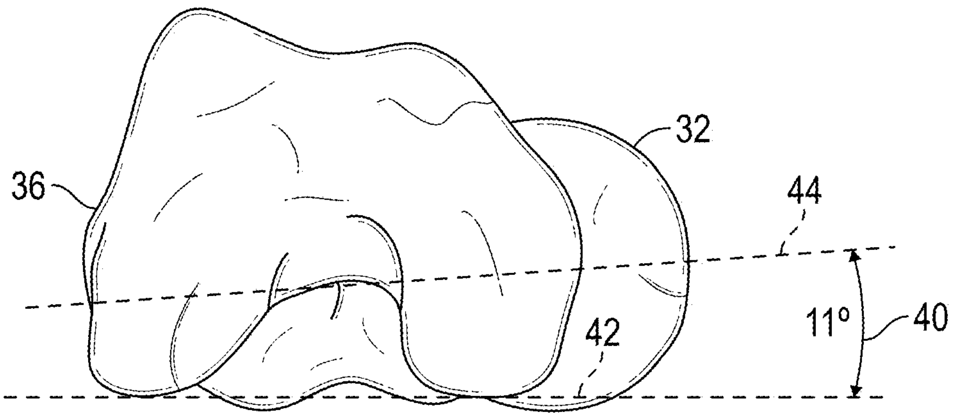
FIG. 3E is bottom-up view of the femur demonstrating normal version of 11°, that has been achieved via spiral guided growth, thus correcting in-toeing and mitigating vs. hip and knee injuries.

As will be described in greater detail below, the groove 128 may enable the second end 112 to be releasably attached to the first end 110. "Releasable" attachment means the attachment of two items together such that they may separate from each other. By design, this may not occur until the rotational growth is affected and the two tethers may be generally parallel to the long axis of the bone (FIG. 3D). When subjected to the considerable distraction force generated by the growth plate (estimated to be 500 Newtons) the two ends may separate, permitting unrestricted growth (FIG. 3G). This may obviate the need to remove the implants. By contrast, "non-releasable" implants must be removed in a timely manner in order to avoid an iatrogenic growth arrest and consequent limb foreshortening.

In alternative embodiments, releasable attachment may be provided by making a tether 102 or coupling member 104 weak enough to break under the desired conditions. For example, the tether 102 may be modified to make the central portion 114 much thinner, and thus breakable under tension. Additionally, or alternatively, the tether 102 may include a central portion 114 that may include a groove 128 configured to reduce the cross-sectional area of the central portion 114. Additionally, or alternatively, the tether 102 may be modified so that the central portion 114 includes one or more holes or perforations to reduce the total cross-sectional area of the central portion 114, one of the holes may be a third aperture 140.

Alternatively, one of the coupling members 104 may be modified to have a breakaway head or the like. Additionally, or alternatively, the tether 102 may be configured so that the cross-sectional area proximate the first aperture 122, the second aperture 126, and/or both the first aperture 122 and the second aperture 126 may be less than the cross-sectional area of the central portion 114, thus the area proximate the first aperture 122, the second aperture 126, and/or both the first aperture 122 and the second aperture 126 may be breakable under tension. Additionally, or alternatively, the material included in the central portion 114 may be selectively annealed to reduce the tensile strength, thus breakable under tension.

The tether 102 may be configured to separate when a tension force of 300 N to 700 N is applied to opposite ends of the tether 102. Further, the tether 102 may be configured to separate when a tension force of 400 N to 600 N is applied to opposite ends of the tether 102. Still further, the tether 102 may be configured to separate when a tension force of 450 N to 550 N is applied to opposite ends of the tether 102. In some embodiments, tether 102 may be configured to separate when a tension force of 500 N is applied to opposite ends of the tether 102.

Figure 4A:
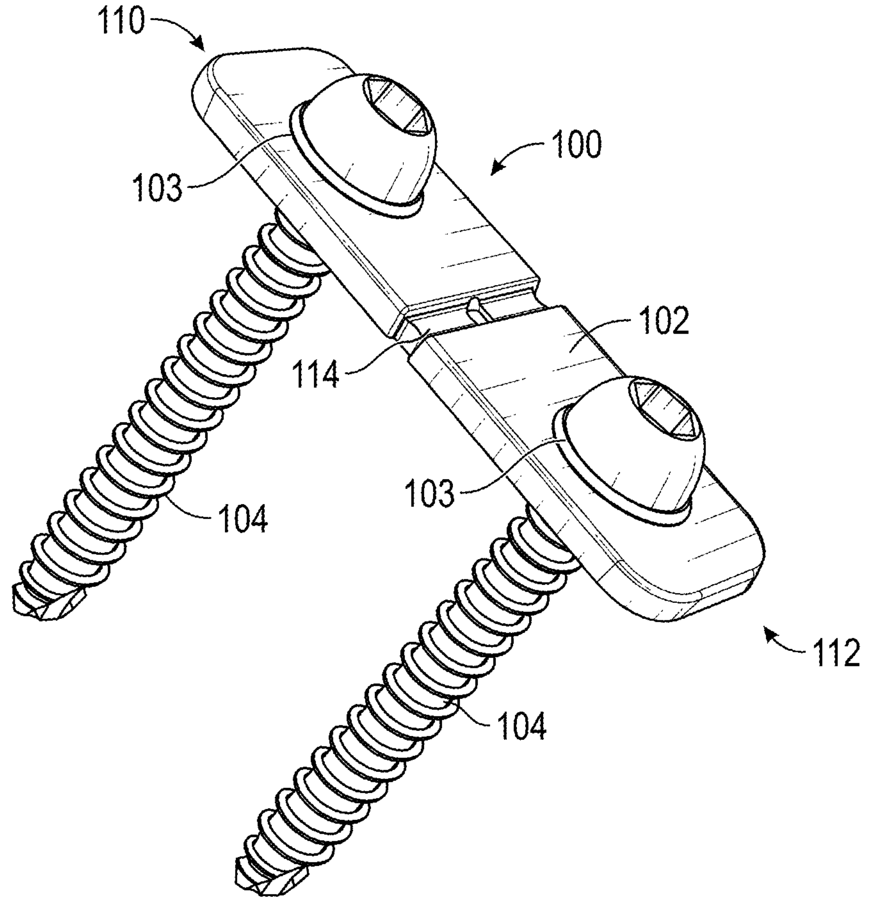
FIG. 4A is a perspective view of a tether assembly with coupling members according to one embodiment.

Referring to FIG. 4A, the tether 102 may further have a third aperture 140 positioned approximately at the mid-point of the central portion 114. The third aperture 140 may be used to position the tether 102 centrally over the physis 60 by aligning the third aperture 140 with the physis 60. This may be done visually by a surgeon installing the tether 102, for example, by ensuring that third aperture is radiographically aligned with the physis and positioned obliquely before securing it to the bone. Additionally, or alternatively, a temporary guidewire or other instrument may be registered on or near the physis 60 and inserted through the third aperture 140 and into contact with the physis 60 to guide placement of the tether 102 such that the third aperture 140 is placed on or near the physis 60.

Relative to the longitudinal axis 72 of the femur, the tether(s) may be oriented obliquely by the degree of desired rotational correction (often 20°-30°).

Once the tether 102 has been properly positioned on the femur 58, one of the coupling members 104 may be placed through the one of the grommets 103 located within the first aperture 122 to couple the tether 102 to the anterior portion of the metaphyseal portion 64 of the femur 58, proximal to the physis 60. Another of the coupling members 104 may be placed through another one of the grommets 103 located within the second aperture 126 to couple the tether 102 to the posterior portion of the epiphyseal portion 62, distal to the physis 60 and posterior to the first end 110. The coupling members 104 may advantageously be placed a minimum distance of 6 mm to 8 mm away from the central portion of the physis 60 to ensure that the coupling members 104 do not impede or interfere with the natural growth emanating from the physis 60. In alternative embodiments, the tether 102 may be reversed, such that the first end 110 is secured to the metaphyseal portion 64 and the second end 112 is secured to the epiphyseal portion 62.

Additionally, or alternatively, a first tether 102 may be secured to the femur 58 such that the first end 110 is secured to the metaphyseal portion 64 and the second end 112 is secured to the epiphyseal portion 62 and a second tether 102 may be oriented obliquely and secured to the opposite side of the femur 58 such that the first end 110 is secured to the epiphyseal portion 62 and the second end 112 is secured to the metaphyseal portion 64, wherein one of the tethers 102 may be secured to the medial side of the femur 58 and the other of the pair of the tethers 102 may be secured to the lateral side of the femur 58. In another embodiment, a pair of oblique tethers 102 may be secured to a tibia in a similar manner as described for the femur.

FIG. 3A shows a medial view of the femur with a pair of oblique tethers applied. This angle θ is the amount of anteversion in excess of the normal anteversion angle of 11°. The angle θ may be the anteversion angle 50 of FIG. 3C minus the anteversion angle 40 (11°) of FIG. 1C. It is desirable to correct the rotational deformity by rotating the distal end of the femur 58 by e° relative to the proximal end of the femur 58, so that the posterior condyles of the femur 58 are restored to a normal alignment with the femoral neck and head of the femur 58. To ensure that the induced rotational change in the femur 58 is radially symmetric, a mirror image second tether assembly may be placed obliquely on a second side of the femur 58. In the case of the distal end of the femur 58, the second tether assembly may be placed on the lateral side of the femur 58, opposite and radially symmetrical to the placement of the tether assembly 100 on the medial side as shown in FIGS. 3A and 3B.

FIGS. 3A and 3B illustrate the femur 58 and the tether assembly 100 at the time of a surgery in which the tether assembly 100. Optionally, additional tether assemblies 100) may be installed (for example, on the tibia). FIGS. 3D and 3E Illustrate the femur 58 and tether assembly 100 shown in FIGS. 3A and 3B after induced spiral growth has corrected the malrotation. Following the application of dual oblique tethers, growth may follow a spiral pattern, correcting the malrotation. When the tethers are generally vertically oriented, they may intentionally "fail" when subjected to the considerable force generated by the growth plate.

FIG. 3D is a medial view of a right femur with the tether assembly of FIG. 3A, depicting correction of malrotation because tethers have induced spiral growth while assuming a vertical position. FIG. 3E is bottom-up view of the femur demonstrating normal version of 11°, that has been achieved via spiral guided growth, thus correcting in-toeing and mitigating vs. hip and knee injuries. Upon reaching the terminal alignment of B°, the changed alignment (relative to the transverse plane) of the tether is such that the tension force applied to the tether 102, by the coupling members 104 and the grommets 103, is at or near a peak, resulting in separation of the tether 102.

Figure 3F:
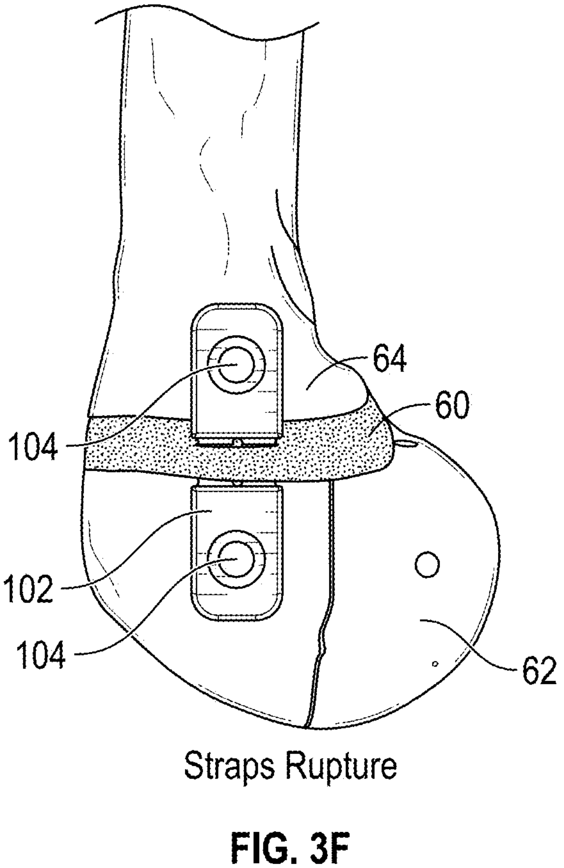
FIG. 3F illustrates intentional fatigue of the vertical tethers, consequent to the powerful forces of growth generated by the physis.
Figure 3G:
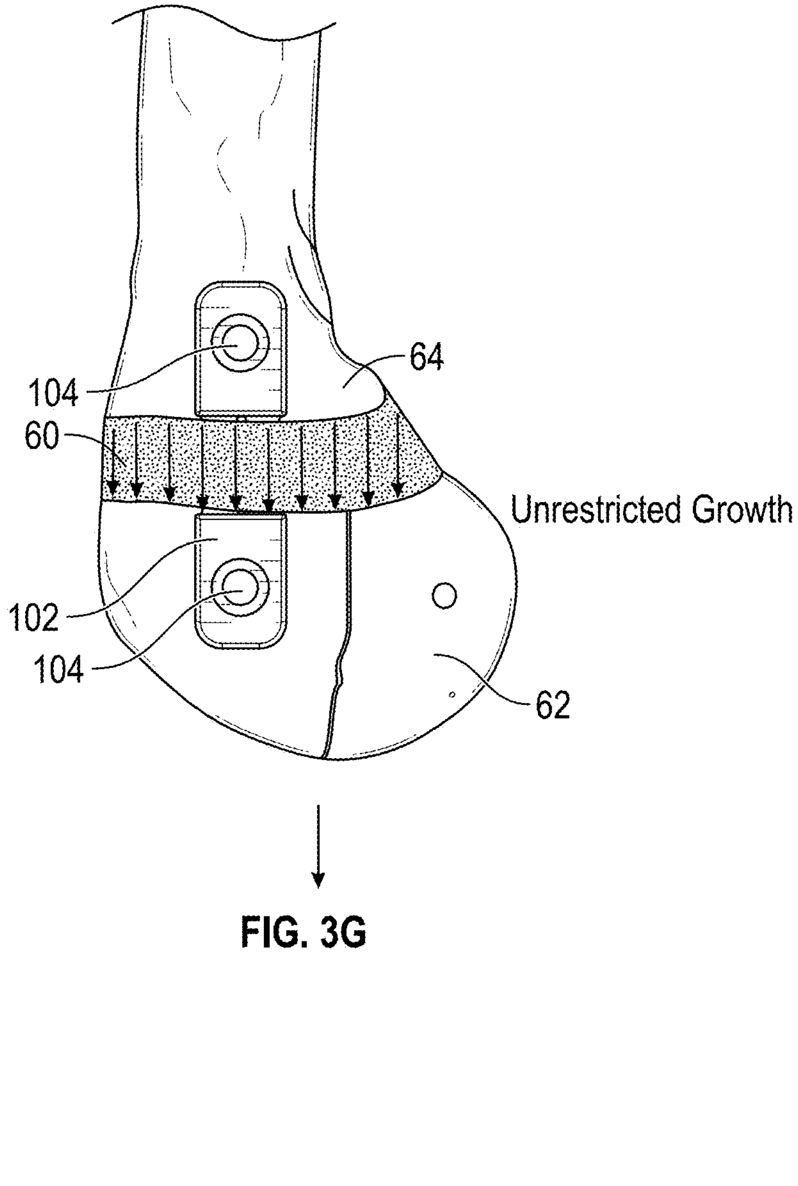
FIG. 3G illustrates each tether separates into two parts, permitting uninterrupted longitudinal growth. Implant removal is optional.

FIG. 3F illustrates intentional fatigue of the vertical tethers, consequent to the powerful forces of growth generated by the physis. FIG. 3G illustrates each tether separates into two parts, permitting uninterrupted longitudinal growth. Implant removal is optional. This is designed to release the tether 102 from attachment to the epiphyseal portion 62 and/or the metaphyseal portion 64, thereby permitting uninterrupted growth of the untwisted femur 58 (FIG. 3G).

The amount of rotational correction as measured by the angle θ can be "programmed" into the surgical technique by selecting the right combination of a, B, and the distance 150 between the first aperture 122 and the second aperture 126 of the tether 102 (referred to herein as "plate length") for a given diametrical width of a distal femur.

It may be advantageous to provide an "automated" release of the constraint imposed by the tether 102 once the rotational deformity in the femur 58 is corrected and before the tether 102 migrates to a vertical alignment with respect to the transverse plane. If the tether 102 were to continue to constrain the distance between the coupling members 104 as it achieved vertical alignment, the tether 102 would arrest further longitudinal growth of the femur 58. Indeed, such a constraint is known in the clinical literature as "shutting down the growth plate," a condition that permanently eliminates the ability of the growth plate, or physis 60, to generate new bone to continue the natural growth of the bone. Such a clinical condition can be very deleterious to the child, as it could lead to leg length discrepancies or failure to achieve normal height in adulthood. The tether assembly 100 may be configured so that the tension force required to separate the tether 102, and generally eliminate the constraint imposed by the tether 102, may be less than the maximum force exerted by the physis 60 during natural growth of the bone.

Figure 4B:
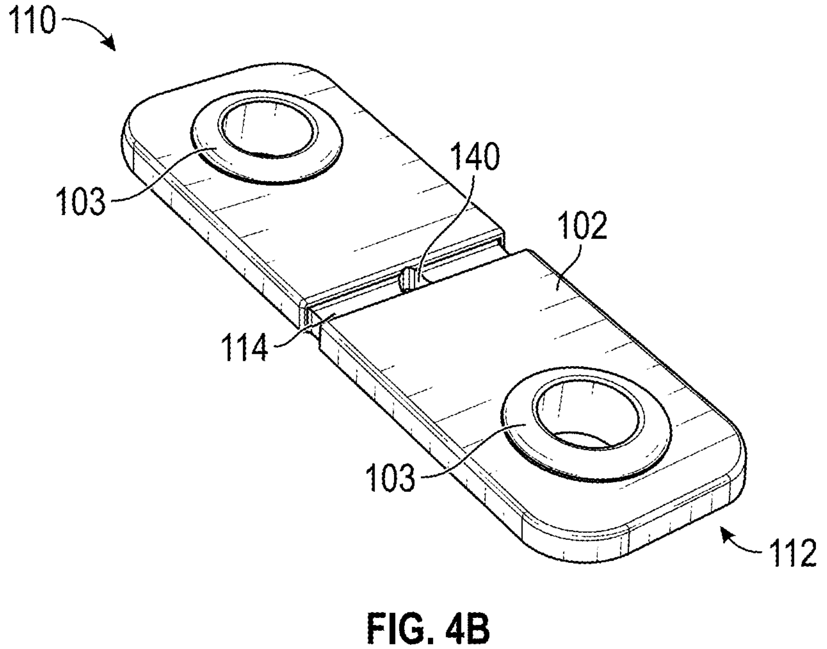
FIG. 4B is a perspective view of the tether assembly of FIG. 4A.

FIG. 4A is a perspective view of a tether assembly with coupling members according to one embodiment. FIG. 4B is a perspective view of the tether assembly of FIG. 4A. The coupling members 104 and grommets 103 are positioned in the first aperture 122 and the second aperture 126. The flexible tether 102 may self-contour to match that of the medial or lateral epicondylar bone surface, on which the tether 102 is to be attached (FIG. 3B).

Figure 5:
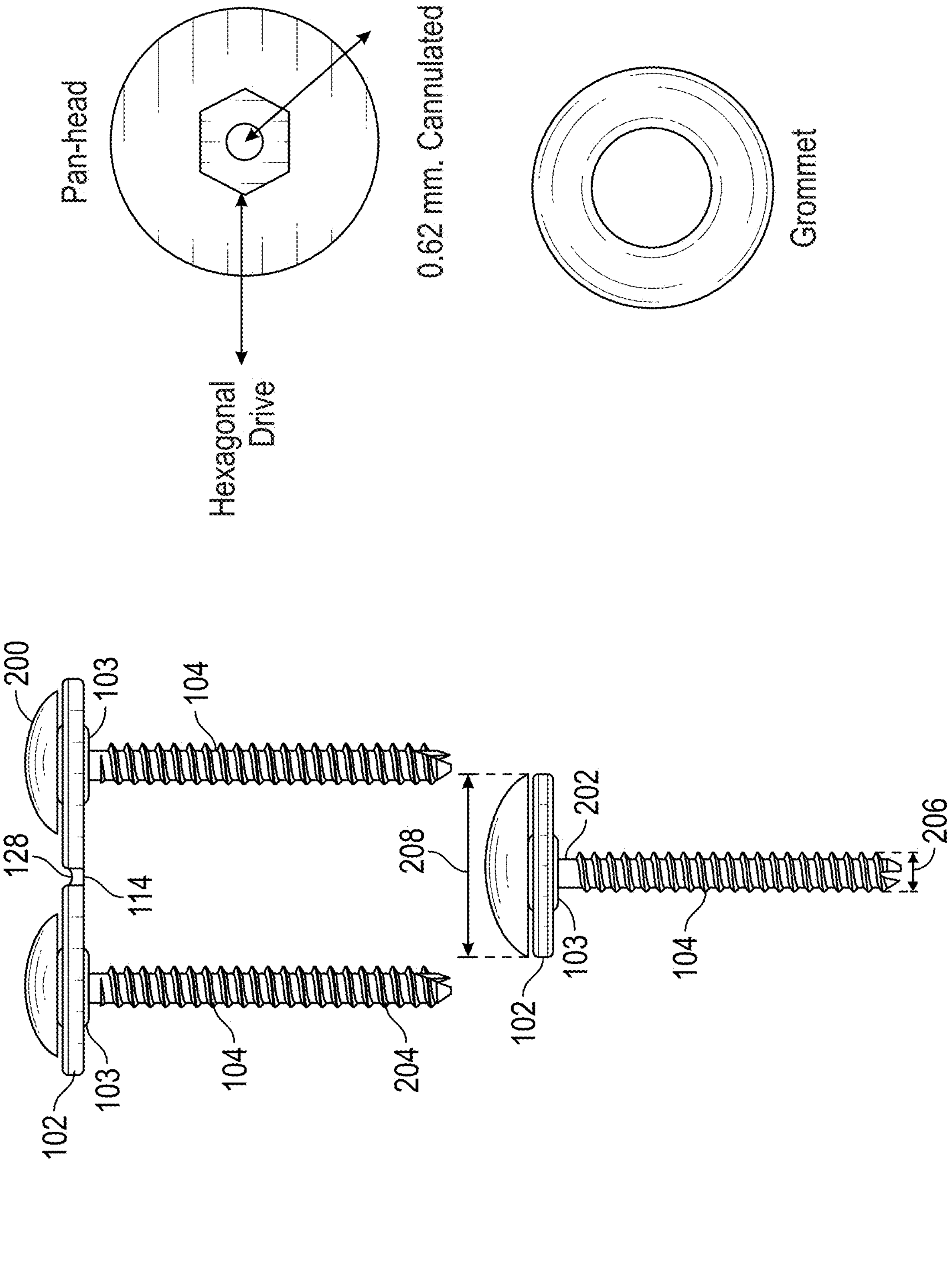
FIG. 5 is a front view and side view of the tether assembly of FIG. 4A, a top view of a fastener of the tether assembly of FIG. 4A, and a top view of a grommet of the tether assembly of FIG. 4A.

FIG. 5 is a front view and side view of the tether assembly of FIG. 4A, a top view of a fastener of the tether assembly of FIG. 4A, and a top view of a grommet of the tether assembly of FIG. 4A. Each of the coupling members 104 may be a bone screw or other bone fastening device of any type known in the orthopedic arts. As shown, each of the coupling members 104 may have a head portion 200 and a shank portion 202 extending from the head portion 200. The shank portion 202 may have a plurality of bone engagement features extending therefrom. As embodied in FIG. 7A, FIG. 7B and FIG. 8, the bone engagement features may be configured as screw threads 204.

Furthermore, the threshold force may be selected such that it induces a corresponding restraining force on the physis 60 that is below the force that would induce growth from the physis 60 to "shut down."

One of the coupling members 104 may include a thread diameter 206 and a head portion 200 including a head width 208, shown in FIG. 5. One of the grommets 103 may be configured with a greater thickness than the tether 102. One or more of the grommets 103 may have a top surface that may lie above a top surface of the tether 102 when the one or more grommets 103 is received within one of the first aperture 122 and the second aperture 126. Additionally, one or more of the grommets 103 may have a bottom surface that may lie below a bottom surface of the tether 102 when one or more the grommets 103 is received within one of the first aperture 122 and the second aperture 126. The thread diameter 206 may be configured to slidably pass through the one or more grommets 103. The head width 208 may be configured to engage the top surface of the one or more grommets 103.

The one or more grommets 103 may lie adjacent to the surface of the femur 58. The one or more coupling members 104 may lie adjacent to a top surface on the one or more grommets 103. The coupling members 104 may secure the grommets 103 directly to the surface of a bone, thereby allowing movement and/or rotation of the tether 102 relative to one or more coupling members 104 without resulting in a torsional force being applied to the one or more coupling members 104.

FIG. 6 is a table 250 illustrating the start angle α (in degrees) and approximate treatment time (in months) that correspond to a rotational correction angle θ (in degrees), an average distal femur width (in mm) for a given length plate (in mm). The plate length provided in the table 250 is the distance 150 between a center of the first aperture 122 and a center of the second aperture 126.

All of the values in the table 250 are based on a constant end angle β of 70°. Using analytical geometry, similar tables can be developed for other values of end angle, start angle, treatment time, femur width, rotational correction angle and plate lengths as needed. For more severe deformities than provided in the table 250, multiple treatments may be applied to the same patient. For example, for a patient having 35° of rotational deformity and a 54 mm femur width, the surgeon can apply the tether 102 at a start angle of 43° to achieve 20° of rotational correction in approximately 7 months. Then in a subsequent surgical procedure, the surgeon can remove and reapply the coupling members 104 and the tether 102 (or a tether 102 with a different size and/or contour) at a start angle of 52° to achieve another 15° of rotational correction in approximately 5 months. Thus, the patient undergoes a total of 35° of rotational correction in approximately 12 months.

Figure 7B:
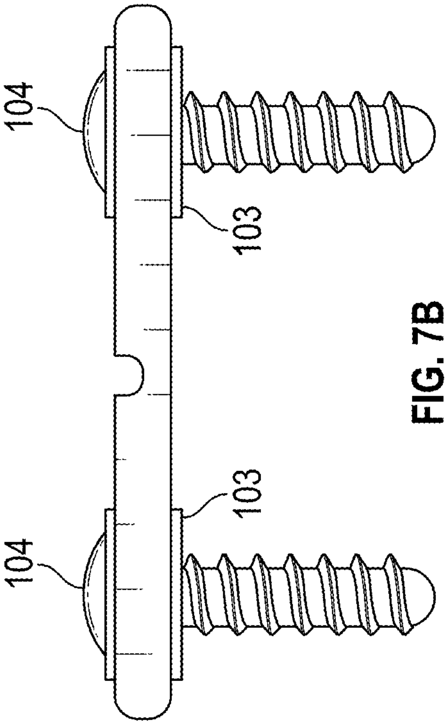
FIG. 7B is a partial side view of the tether assembly of FIG. 7A with coupling members.
Figure 7A:
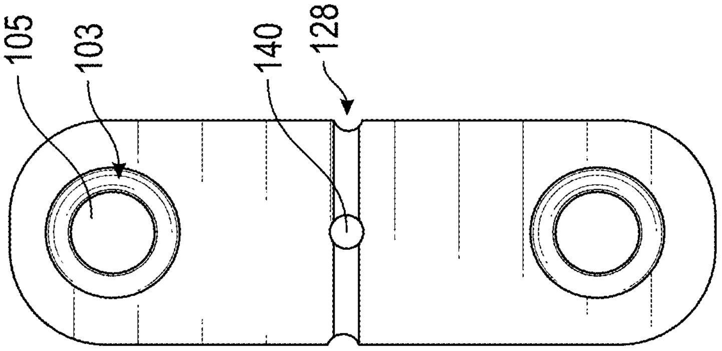
FIG. 7A is a top view of a tether assembly according to one embodiment.

FIG. 7A is a top view of a tether assembly 100 according to one embodiment. FIG. 7B is a partial side view of the tether assembly 100 of FIG. 7A with coupling members. In an embodiment, the tether 102 may have a width between 8 mm and 16 mm. Further, the tether 102 may have a width between 10 mm and 14 mm. Still further, the tether 102 may have a width of approximately 12 mm.

In an embodiment, the tether 102 may have a thickness between 1 mm and 3 mm. Further, the tether 102 may have a thickness between 1.5 mm and 2.5 mm. Still further, the tether 102 may have a thickness of approximately 2 mm.

The one or more grommets 103 may have a grommet aperture 105. The grommet aperture 105 may be larger than the thread diameter 206 and smaller than the head width 208 of the one or more coupling members 104 so that the one or more grommets 103 may receive the threaded portions on the one or more coupling members 104.

Figure 8:
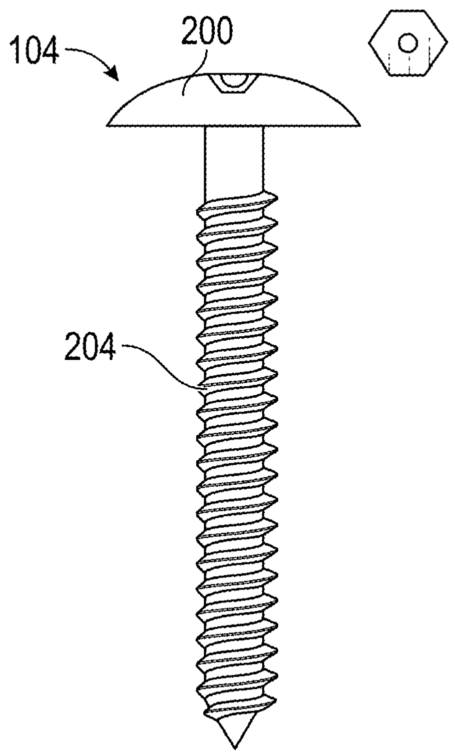
FIG. 8 is a front view of the coupling member of FIG. 7B.

FIG. 8 is a front view of the coupling member 104 of FIG. 7B. The one or more coupling members 104 may be configured as a pan head type screw. The self-tapping screw may be cannulated (1.6 mm) in order that it may be accurately inserted over a smooth guide wire. The proximal 4 mm. of the shank is smooth, without threads. The intent may be for the screw to provide secure fixation to the bone without compression of the tether against it. This may foster swiveling of the tethers, guiding spiral growth.

The screw threads 204 may be configured with a cortical engaging thread form, a cancellous engaging thread form, or a combination of the two. The one or more coupling members 104 may include a cortical engaging thread form and/or cancellous engaging thread form know in the orthopedic arts. The one or more coupling members 104 may further include a drive features (such as a hex, a hexalobe, a square, or other drive feature known in the orthopedic arts) and a self-drilling/self-tapping tip.

Figure 9A:
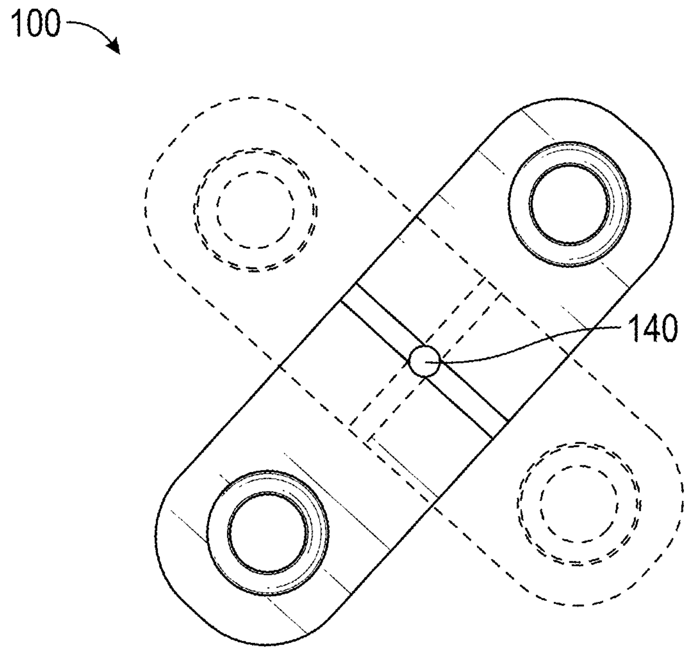
FIG. 9A is a top view of a mounted pair of tether assemblies of FIG. 7A.
Figure 9B:
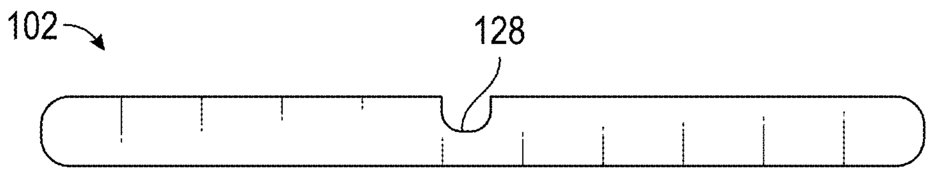
FIG. 9B is a side view of a tether of the tether assembly of FIG. 7A.

FIG. 9A is a top view of a mounted pair of medial and lateral tether assemblies 100 of FIG. 7A. FIG. 9B is a side view of a tether 102 of the tether assembly 100 of FIG. 7A. A first tether 102 may be secured to the femur 58 or a tibia such that the first end 110 is secured to the metaphyseal portion 64 and the second end 112 is secured to the epiphyseal portion 62 and a second tether 102 may be oriented mirror image obliquely and secured to the opposite side of the femur 58 or tibia such that the first end 110 is secured to the epiphyseal portion 62 and the second end 112 is secured to the metaphyseal portion 64, wherein one of the pair of the tethers 102 may be secured to the medial side of the femur 58 or tibia and the other of the pair of the tethers 102 may be secured to the lateral side of the femur 58 or tibia.

The pair of tether assemblies 100 may be positioned so that the third aperture 140 of the first tether 102 is aligned with the third aperture 140 of the second tether 102. When secured as an oblique pair of tether assemblies 100 as described, the tether assemblies 100 may rotate to near vertical, while passively inducing the desired rotational correction.

Figure 10:
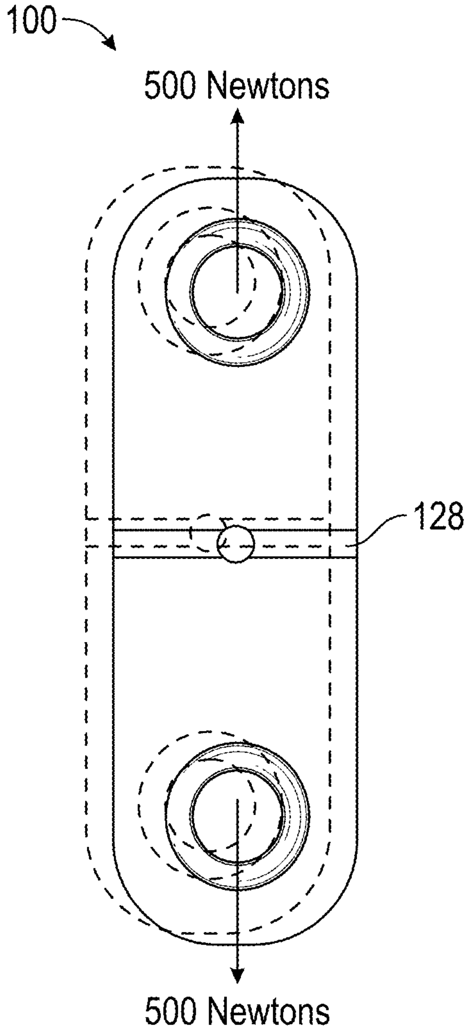
FIG. 10 is a top view of the pair of tether assemblies of FIG. 9A after a first period of bone growth.

FIG. 10 is a top view of the pair of tether assemblies 100 of FIG. 9A after a first period of induced spiral bone growth. As the epiphysis continues to grow away from the metaphysis, the tether may separate, through its narrow midsection, into two separate portions. The pair of tether assemblies 100 shown in FIG. 9A may rotate to near vertical and the force applied to the pair of tether assemblies 100 by the physis may near a maximum. A first portion of bone may apply a force to the tether 102 in a generally superior direction. A second portion of bone may apply a force to the tether 102 in a generally inferior direction.

Figure 11:
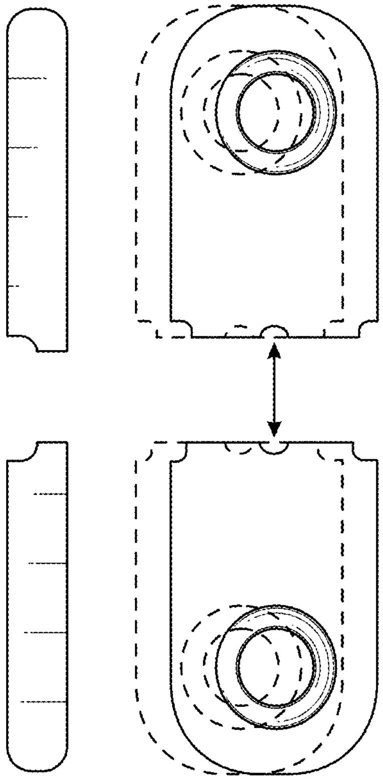
FIG. 11 is a top view of the pair of tether assemblies of FIG. 9A after a second period of bone growth.

FIG. 11 is a top view of the pair of tether assemblies 100 of FIG. 9A after a second period of bone growth. After a second period of time following a surgery, the force applied to the pair of tether assemblies 100 by the physis (growth plate) may exceed the tensile strength of the tether 102 causing separation of the tether 102 thereby permitting the femur 58 or tibia to elongate without further rotational adjustment and generally eliminating the resistance applied to the physis by the pair of tether assemblies 100. The separation of the pair of tether assemblies 100 may avoid growth arrest if the pair of tether assemblies 100 may not be removed through a second surgical intervention. Additionally, the separation of the pair of tether assemblies 100 may avoid iatrogenic limb foreshortening. Surgical removal of the pair of tether assemblies 100 may be optional.

Figure 12:
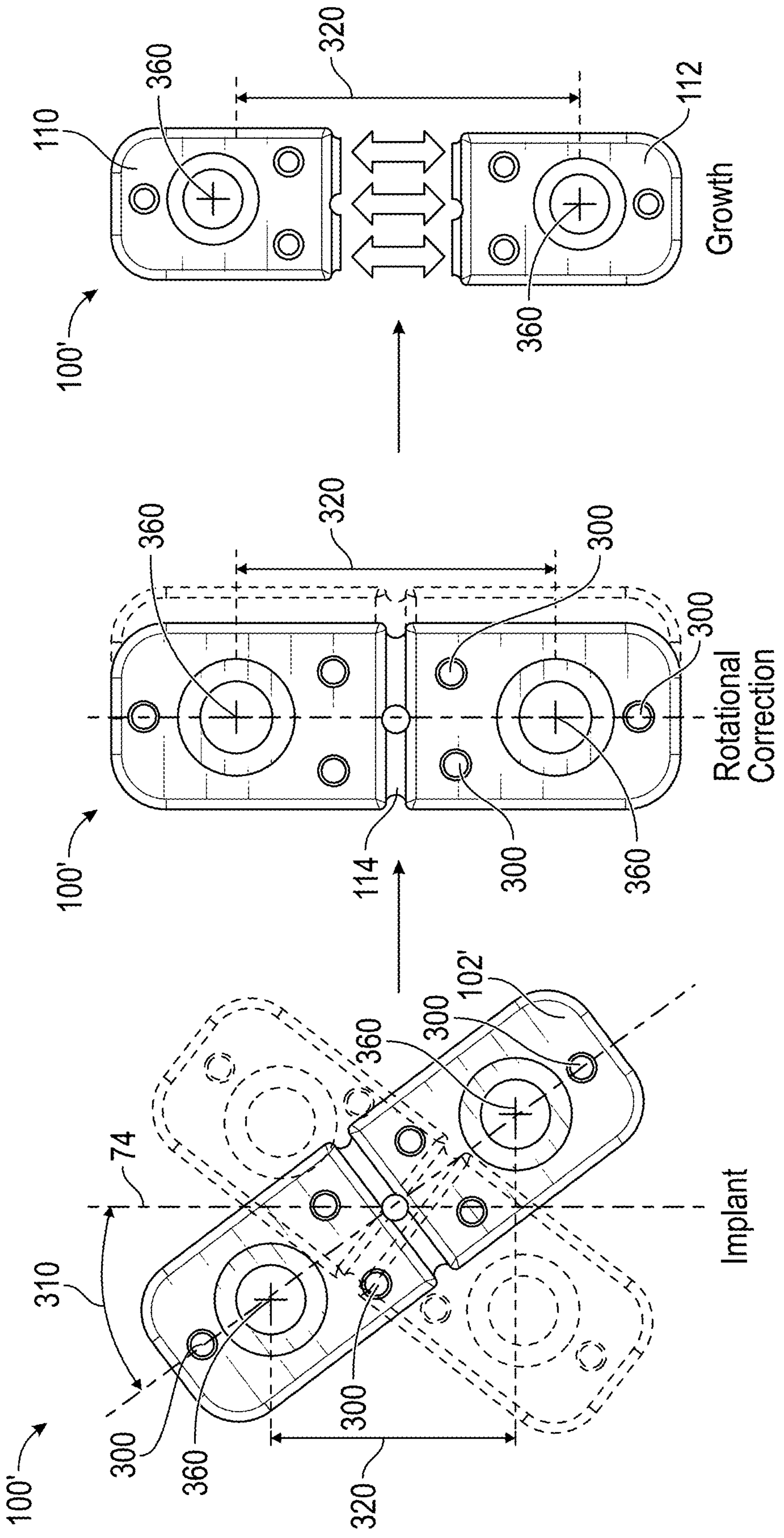
FIG. 12 is a front view of a tether assembly at three different stages of implantation according to an embodiment of the present disclosure.

FIG. 12 is a front view of a tether assembly 100' at three different stages of implantation according to an embodiment of the present disclosure. Various parts of the tether assembly 100' may be identical or similar to their counterparts on the tether assembly 100 and/or other tether assembly embodiments presented herein. These parts may not be described again here. All statements made regarding the tether assembly 100 apply to the tether assembly 100' unless they would be contradicted by the differences between the two. The tether assembly 100' may be configured to support radiostereometric analysis of growth of the physis 60 and/or rotation of the epiphyseal portion 62 relative to the metaphyseal portion 64.

Radiostereometric analysis is well known in the art as a highly accurate technique for the assessment of three-dimensional movement of bones and/or portions of bones. Radiostereometric analysis may also be used as a highly accurate technique for the assessment of three-dimensional movement of an implants and/or portions of implants, when the implant and/or portions of implants may be secured to a bone and/or portions of bones.

The tether assembly 100' may include three or more radiopaque beads 300. The radiopaque beads 300 may be configured as markers for radiostereometric analysis of the growth plate. The radiopaque beads 300 may be manufactured from radiopaque material such as tantalum. Other radiopaque materials may also be used, such as stainless steel, titanium, and/or tungsten. Alternatively, a radiolucent material including a radiopaque additive, such as barium sulfate, bismuth subcarbonate, bismuth trioxide, and/or bismuth oxychloride may be used.

The radiopaque beads 300 may be radiopaque beads and may have a generally spherical shape. The generally spherical shape may facilitate determination of a center point, and therefore a specific point in three-dimensional space, of each radiopaque bead 300 regardless of the radiographic angle.

The tether assembly 100' may include two sets of radiopaque beads 300. Each set of radiopaque beads 300 may include a minimum of three radiopaque beads 300 but may include more. The three radiopaque beads 300 in each set may be arranged in a triangular pattern. The triangular pattern of three radiopaque beads 300 may function as a fiducial array to define a specific point in three-dimensional space.

Each set of radiopaque beads 300 may include a set central point 360. A first set of radiopaque beads 300 may be included in a first end 110 of the tether assembly 100' and a second set of radiopaque beads 300 may be included in a second end 112 of the tether assembly 100'. Thereby, movement of the first end 110 may be calculated independently of the second end 112 after separation of the tether assembly 100' at the central portion 114 into two portions.

The radiopaque beads 300 may be embedded in the front of the tether assembly 100', embedded in the back of the tether assembly 100', and/or over-molded within the tether assembly 100' so that the radiopaque beads 300 beads may be inside the tether 102'. The radiopaque beads 300 may be fixed relative to the tether 102' so that the position of each of the radiopaque beads 300 also remains fixed relative to the locations of the other radiopaque beads 300 within the set of three (or more) and relative to the set central point 360.

The tether assembly 100' may include an implant reference distance 320. The implant reference distance 320 may be the distance between a first set central point 360 included in the first end 110 and a second set central point 360 included in the second end 112. As the physis grows and/or the tether assembly 100' separates into two portions, the implant reference distance 320 may increase. The increase in the implant reference distance 320 may correlate to the growth of the physis and/or rotation of the epiphyseal portion 62 relative to the metaphyseal portion 64.

Figure 13:
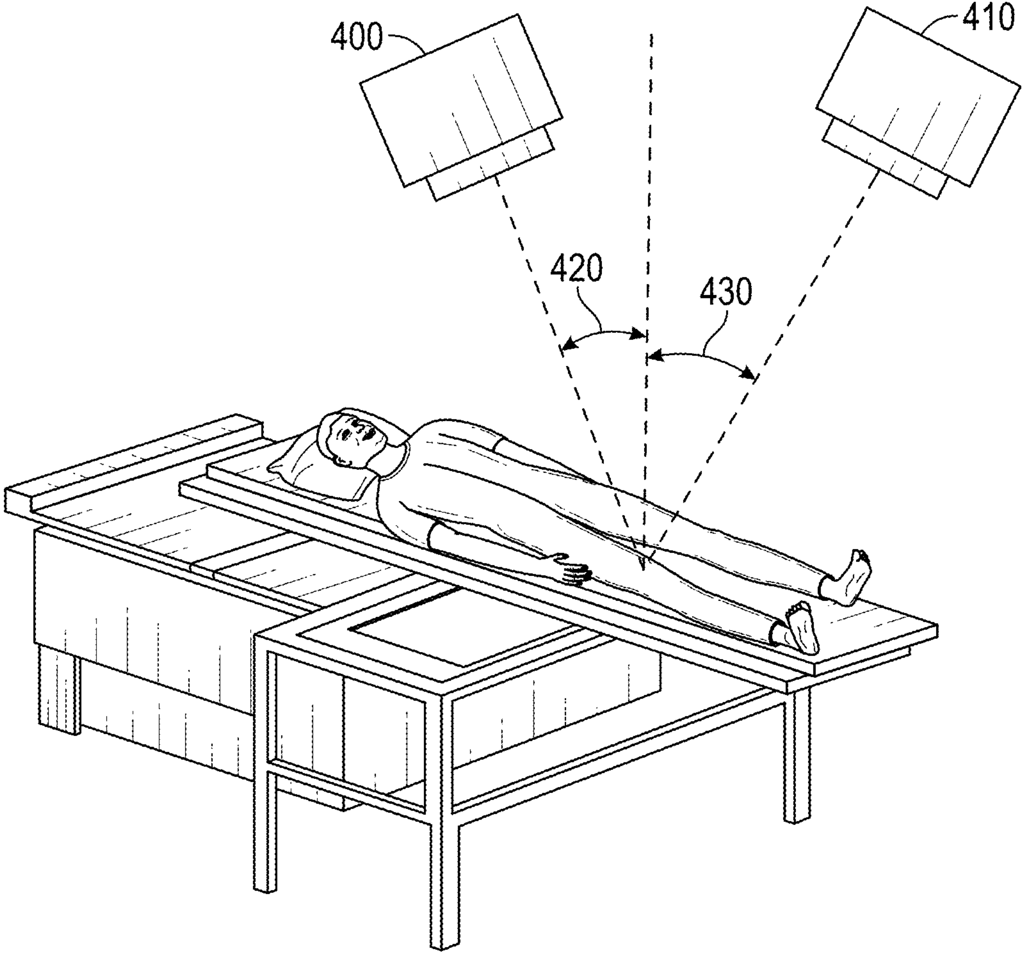
FIG. 13 is a perspective view of an exemplary radiostereometric examination set-up.

FIG. 13 is a perspective view of an exemplary radiostereometric examination set-up. Radiostereometric analysis may include radiographic imaging from at least two different angles. A first radiographic source 400 may be directed to a patient at a first radiographic angle 420. A second radiographic source 410 may be directed to a patient at a second radiographic angle 430. The first radiographic angle 420 may be set between 30 degrees and 60 degrees. The second radiographic angle 430 may be set between 30 degrees and 60 degrees so that an angle measured between the first radiographic angle 420 and the second radiographic angle 430 is between 60 degrees and 120 degrees.

By measuring the distances between the sets of radiostereometric beads and compiling the measurements from the at least two different imaging angles, the location of each set of radiostereometric beads may be determined in a three-dimensional space. The location in the three-dimensional space may then be compared to a baseline (radiostereometric analysis conducted not long after implantation) and/or a previously radiostereometric analysis determined location to calculate the rotation of the epiphyseal portion relative to the metaphyseal portion and/or the longitudinal growth of the physis. Growth of the physis and/or rotation of the epiphyseal portion relative to the metaphyseal portion may also be calculated after separation of the tether assembly 100' has occurred and the physis continues to grow.

Figure 14:
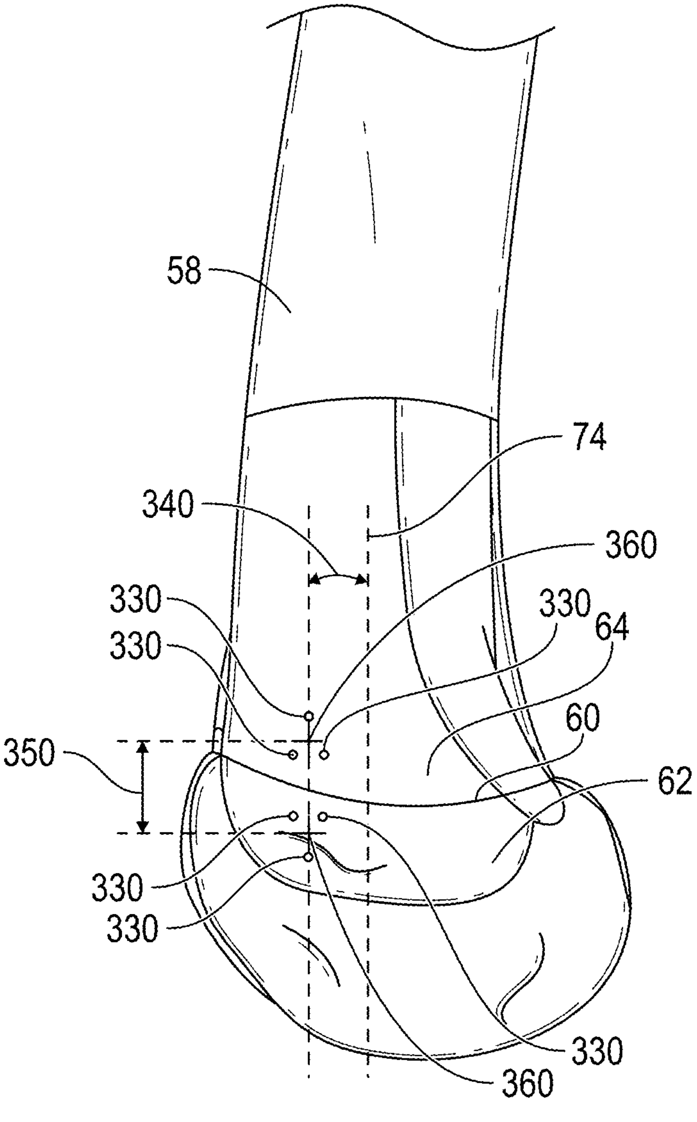
FIG. 14 is a medial view of a right femur with radiostereometric beads according to an embodiment of the present disclosure.

FIG. 14 is a medial view of a right femur 58 with bone radiostereometric beads 330 according to an embodiment of the present disclosure. The bone radiostereometric beads 330 may be placed within a bone in two or more sets to support radiostereometric analysis of growth of the physis 60 and/or rotation of the epiphyseal portion 62 relative to the metaphyseal portion 64.

The bone radiostereometric beads 330 may be manufactured from radiopaque material such as tantalum. Other radiopaque materials may also be used, such as stainless steel, titanium, and/or tungsten. Alternatively, a radiolucent material including a radiopaque additive, such as barium sulfate, bismuth subcarbonate, bismuth trioxide, and/or bismuth oxychloride may be used.

The bone radiostereometric beads 330 may be radiopaque beads and may have a generally spherical shape. The generally spherical shape may facilitate determination of a center point, and therefore a specific point in three-dimensional space, of each bone radiostereometric bead 330 regardless of the radiographic angle.

The epiphyseal portion 62 may receive at least one set of bone radiostereometric beads 330. The metaphyseal portion 64 may also receive at least one set of bone radiostereometric beads 330. Each set of bone radiostereometric beads 330 may include a minimum of three bone radiostereometric beads 330 but may include more. The three bone radiostereometric beads 330 in each set may be arranged in a triangular pattern. The triangular pattern of three bone radiostereometric beads 330 may function as a fiducial array to define a specific point in three-dimensional space.

Each set of bone radiostereometric beads 330 may include a set central point 360. Movement in three-dimensional space of the epiphyseal portion 62 relative to the metaphyseal portion 64 may be calculated through radiostereometric analysis.

The sets of bone radiostereometric beads 330 may include a bone reference distance 350. The bone reference distance 350 may be the distance between a first set central point 360 included in the epiphyseal portion 62 and a second set central point 360 included in the metaphyseal portion 64. As the physis 60 grows the bone reference distance 350 may increase. The increase in the bone reference distance 350 may correlate to the growth of the physis and/or rotation of the epiphyseal portion 62 relative to the metaphyseal portion 64.

The sets of bone radiostereometric beads 330 may include a bone reference angle 340. The bone reference angle 340 may be the angle between a longitudinal axis 74 and an axis connecting the first set central point 360 included in the epiphyseal portion 62 and the second set central point 360 included in the metaphyseal portion 64. As the physis 60 grows a tether assembly 100' may results in rotation of the epiphyseal portion 62 relative to the metaphyseal portion 64, thereby causing the bone reference angle 340 to increase or decrease. The increase or decrease of the bone reference angle 340 may correlate to the growth of the physis and/or rotation of the epiphyseal portion 62 relative to the metaphyseal portion 64.

Figure 15:
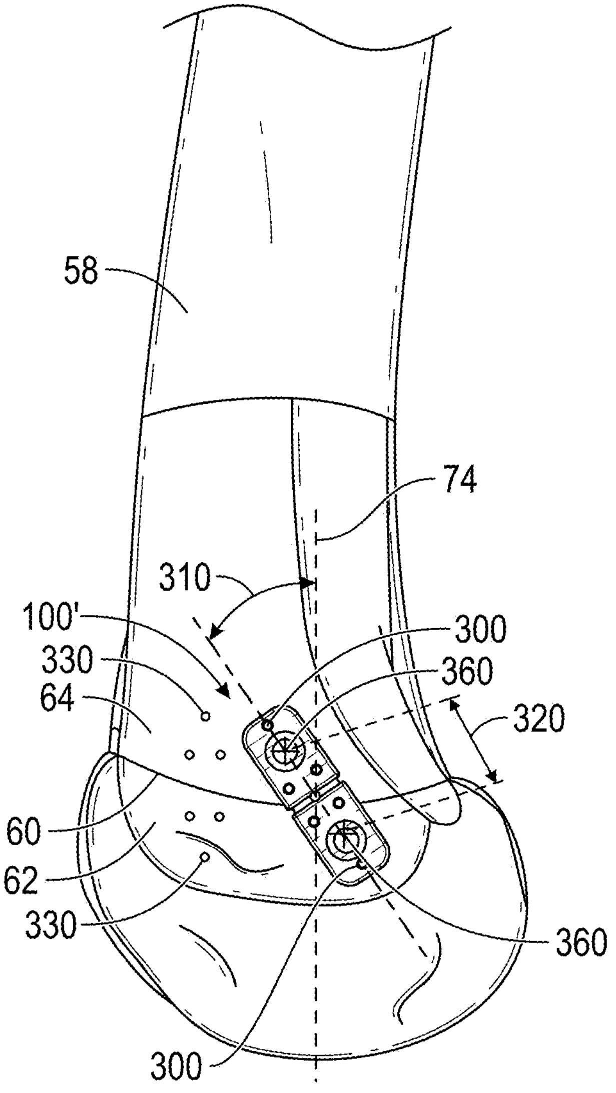
FIG. 15 is a medial view of a right femur with radiostereometric beads and a tether assembly according to an embodiment of the present disclosure.

FIG. 15 is a medial view of a right femur 58 with bone radiostereometric beads 330 and a tether assembly 100' according to an embodiment of the present disclosure. The tether assembly 100' may be implanted at an implant reference angle 310 relative to the longitudinal axis 74. The implant reference angle 310 may be a constant for all patients, or may be selected on a patient-specific basis to control the desired amount of anteversion correction. The implant reference angle 310 may match the desired degree of correction (typically 20°-30°).

A set of bone radiostereometric beads 330 may be placed in both the epiphyseal portion 62 and the metaphyseal portion 64, in addition to implanting a tether assembly 100' that includes a set of radiopaque beads 300 in a first end 110 and a set of radiopaque beads 300 in a second end. Additionally, or alternatively, bone radiostereometric beads 330 and/or the tether assembly 100' having radiopaque beads 300 may be place at more than one location around the femur 58, for example, medially and laterally. Radiostereometric analysis including radiopaque beads 300 and/or implant bone radiostereometric beads 330 at multiple locations around the femur 58 may facilitate assessment of balanced rotation of the epiphyseal portion 62 relative to the metaphyseal portion 64 and/or balanced growth of the physis 60.

Literature in the art has shown that, when using a 2-part fracture model (AO/ASIF type A2) radiostereometric analysis may have an accuracy of +/−2 μm for linear motion in a range of 25 μm to 2 mm and +/−0.015 degrees for rotational motion in a range of 2 degrees to 16 degrees. Radiostereometric analysis may facilitate very accurate measurements of the rate of rotational correction of a distal femur and subsequent longitudinal growth of the physis 60.

Figure 16A:
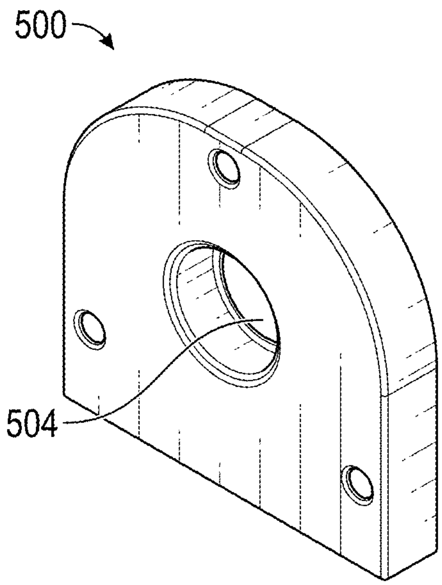
FIG. 16A is a perspective view of a radiostereometric sleeve according to an embodiment of the present disclosure.
Figure 16B:
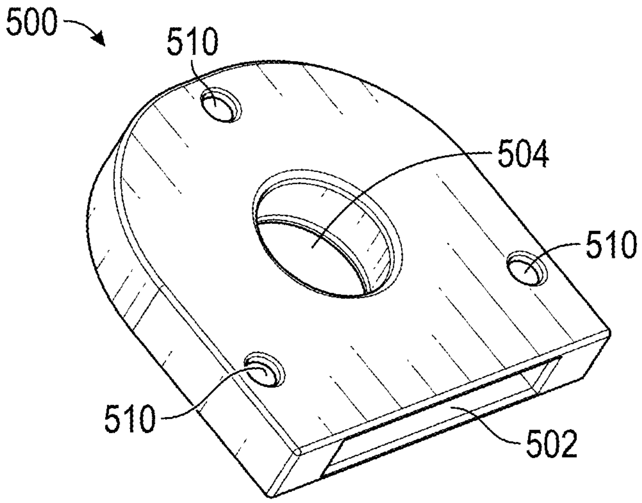
FIG. 16B is a perspective view of the radiostereometric sleeve of FIG. 16A.
Figure 16C:
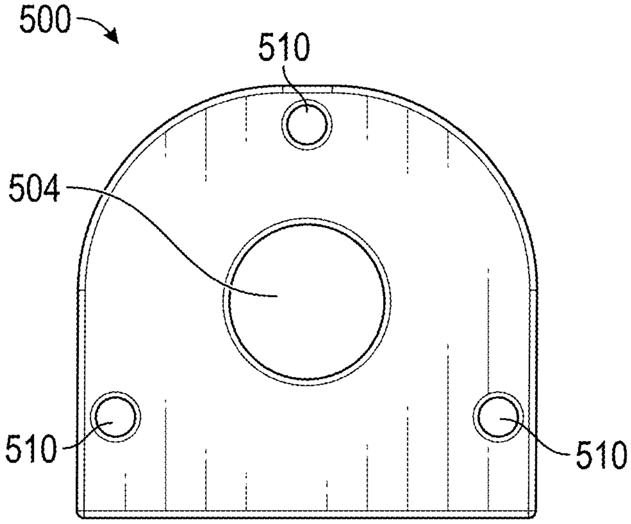
FIG. 16C is a front view of the radiostereometric sleeve of FIG. 16A.
Figure 16D:
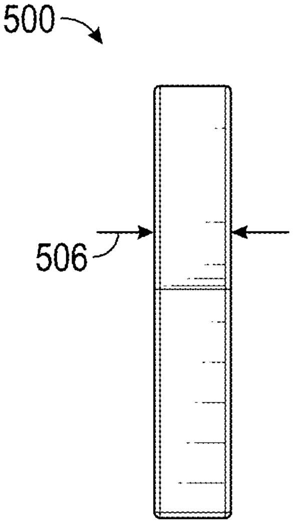
FIG. 16D is a side view of the radiostereometric sleeve of FIG. 16A.

FIG. 16A is a perspective view of a radiostereometric sleeve 500 according to an embodiment of the present disclosure. FIG. 16B is a perspective view of the radiostereometric sleeve 500, FIG. 16C is a front view of the radiostereometric sleeve 500, and FIG. 16D is a side view of the radiostereometric sleeve 500. The radiostereometric sleeve 500 may be configured to receive a first end 110 and/or a second end 112 of a tether assembly 100, thereby facilitating radiostereometric analysis of a tether assembly 100 when the tether assembly 100 does not include radiopaque beads 300.

The radiostereometric sleeve 500 may include an internal portion 502, a central aperture 504, a sleeve width 506, and three or more sleeve radiostereometric beads 510. The internal portion 502 may be configured to receive the first end 110 and/or the second end 112 of the tether assembly 100. When the tether assembly 100 is received within the radiostereometric sleeve 500, the central aperture 504 may align with a grommet aperture 105 of the tether assembly 100 so that a coupling member 104 may pass through the radiostereometric sleeve 500 and the tether assembly 100.

The radiostereometric sleeve 500 may include three or more sleeve radiostereometric beads 510. The sleeve radiostereometric beads 510 may be manufactured from radiopaque material such as tantalum. Other radiopaque materials may also be used, such as stainless steel, titanium, and/or tungsten. Alternatively, a radiolucent material including a radiopaque additive, such as barium sulfate, bismuth subcarbonate, bismuth trioxide, and/or bismuth oxychloride may be used.

The sleeve radiostereometric beads 510 may be radiopaque beads and may have a generally spherical shape. The generally spherical shape may facilitate determination of a center point, and therefore a specific point in three-dimensional space, of each sleeve radiostereometric bead 510 regardless of the radiographic angle.

The three sleeve radiostereometric beads 510 may be arranged in a triangular pattern. The triangular pattern of three sleeve radiostereometric beads 510 may function as a fiducial array to define a specific point in three-dimensional space.

Figure 17A:
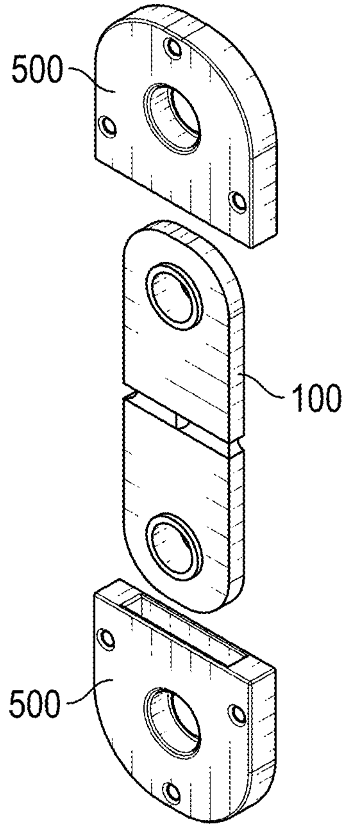
FIG. 17A is an exploded perspective view of the radiostereometric sleeve of FIG. 16A and a tether assembly according to an embodiment of the present disclosure.
Figure 17B:
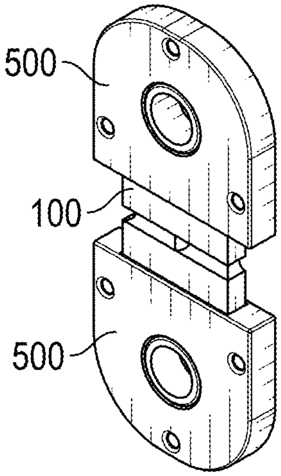
FIG. 17B is a perspective view of the radiostereometric sleeve and the tether assembly of FIG. 17A.
Figure 17C:
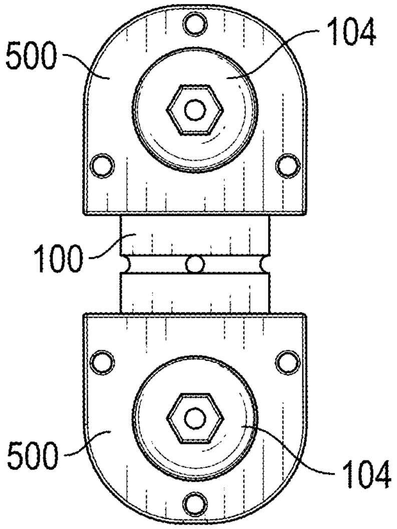
FIG. 17C is a front view of the radiostereometric sleeve and the tether assembly of FIG. 17A with coupling members according to an embodiment of the present disclosure.
Figure 17D:
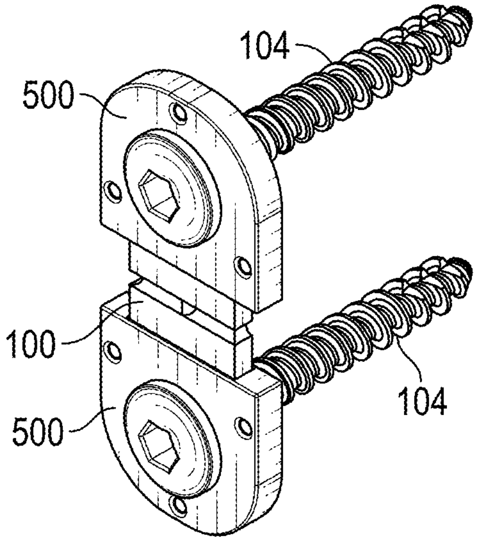
FIG. 17D is a perspective view of the radiostereometric sleeve, the tether assembly, and the coupling members of FIG. 17C.

FIG. 17A is an exploded perspective view of the radiostereometric sleeve 500 and a tether assembly 100 according to an embodiment of the present disclosure. FIG. 17B is a perspective view of the radiostereometric sleeve 500 and the tether assembly 100. FIG. 17C is a front view of the radiostereometric sleeve 500 and the tether assembly 100 with coupling members 104 according to an embodiment of the present disclosure. FIG. 17D is a perspective view of the radiostereometric sleeve 500, the tether assembly 100, and the coupling members 104.

The radiostereometric sleeve 500 may be configured so that with the tether assembly 100 received within the radiostereometric sleeve 500, and the coupling member 104 received in the radiostereometric sleeve 500 and the tether assembly 100, the radiostereometric sleeve 500 is captive on the tether assembly 100. Thereby fixing the location of the sleeve radiostereometric beads 510 relative to the tether assembly 100.

When the tether assembly 100 is implanted with a first radiostereometric sleeve 500 received on the first end 110 and a second radiostereometric sleeve 500 received on the second end 112, the tether assembly 100 may function as previously described for the tether assembly 100' in regards to radiostereometric analysis.

The sleeve width 506 may be sized so that the coupling members 104 may be in direct contact with the grommets 103 and the grommets 103 may be in direct contact with a surface of a bone, thereby allowing the tether assembly 100 to freely rotate as the bone grows and the angle α increases. Since the tether assembly 100 may be allowed to freely rotate, the rotation of the tether assembly 100 may not exert a rotational force on the coupling members 104, thereby reducing the risk of disengaging the coupling members 104 from the bone.

Figure 18A:
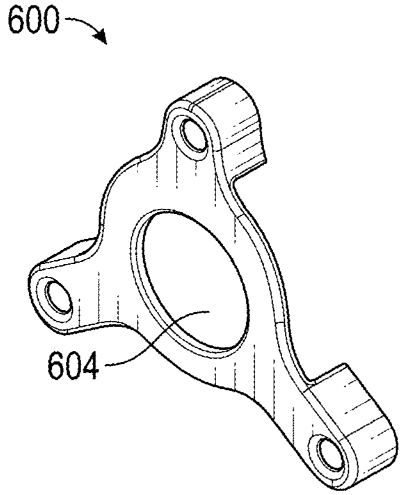
FIG. 18A is a perspective view of a radiostereometric cover according to an embodiment of the present disclosure.
Figure 18B:
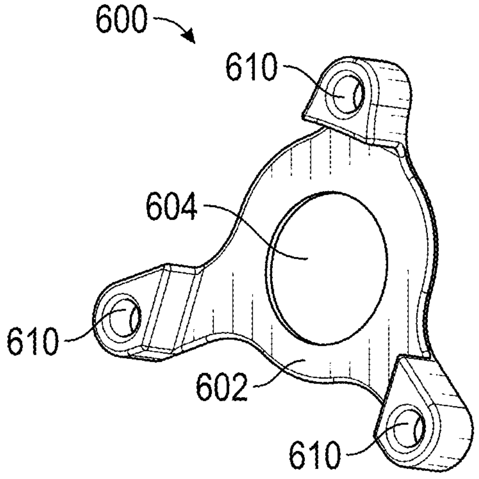
FIG. 18B is a perspective view of the radiostereometric cover of FIG. 18A.
Figure 18C:
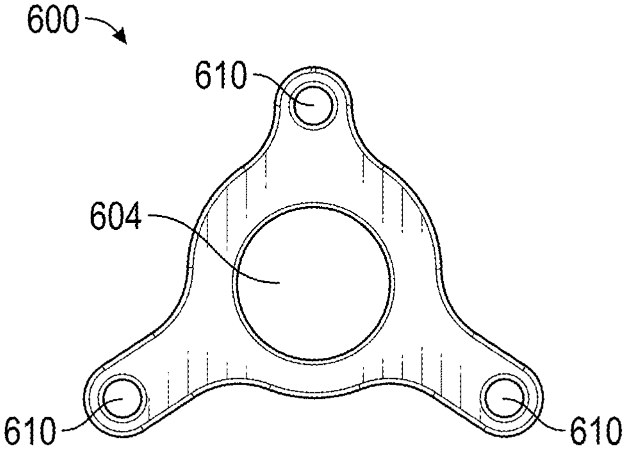
FIG. 18C is a front view of the radiostereometric cover of FIG. 18A.
Figure 18D:
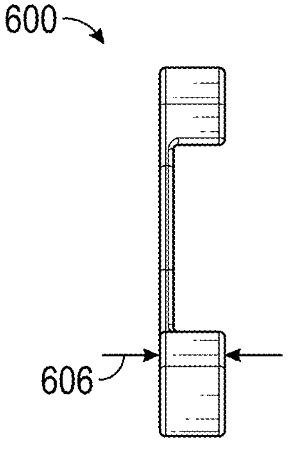
FIG. 18D is a side view of the radiostereometric cover of FIG. 18A.

FIG. 18A is a perspective view of a radiostereometric cover 600 according to an embodiment of the present disclosure. FIG. 18B is a perspective view of the radiostereometric cover 600, FIG. 18C is a front view of the radiostereometric cover 600, and FIG. 18D is a side view of the radiostereometric cover 600. The radiostereometric cover 600 may be configured to receive a first end 110 and/or a second end 112 of a tether assembly 100, thereby facilitating radiostereometric analysis of a tether assembly 100 when the tether assembly 100 does not include radiopaque beads 300.

The radiostereometric cover 600 may include an internal portion 602, a central aperture 604, a cover width 606, and three or more cover radiostereometric beads 610. The internal portion 602 may be configured to receive the first end 110 and/or the second end 112 of the tether assembly 100. When the tether assembly 100 is received within the radiostereometric cover 600, the central aperture 604 may align with a grommet aperture 105 of the tether assembly 100 so that a coupling member 104 may pass through the radiostereometric sleeve 500 and the tether assembly 100.

The radiostereometric cover 600 may include three or more cover radiostereometric beads 610. The cover radiostereometric beads 610 may be manufactured from radiopaque material such as tantalum. Other radiopaque materials may also be used, such as stainless steel, titanium, and/or tungsten. Alternatively, a radiolucent material including a radiopaque additive, such as barium sulfate, bismuth subcarbonate, bismuth trioxide, and/or bismuth oxychloride may be used.

The cover radiostereometric beads 610 may be radiopaque beads and may have a generally spherical shape. The generally spherical shape may facilitate determination of a center point, and therefore a specific point in three-dimensional space, of each cover radiostereometric bead 610 regardless of the radiographic angle.

The three cover radiostereometric beads 610 may be arranged in a triangular pattern. The triangular pattern of three cover radiostereometric beads 610 may function as a fiducial array to define a specific point in three-dimensional space.

Figure 19A:
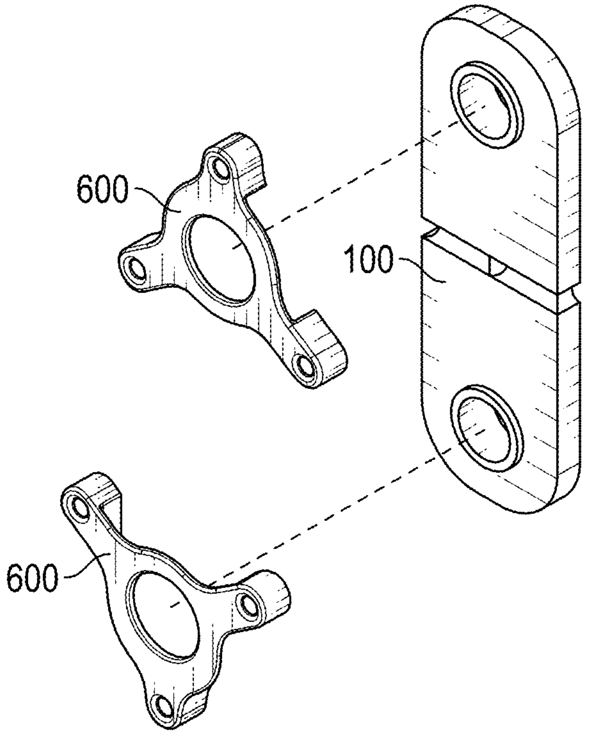
FIG. 19A is an exploded perspective view of the radiostereometric cover of FIG. 18A and a tether assembly according to an embodiment of the present disclosure.
Figure 19B:
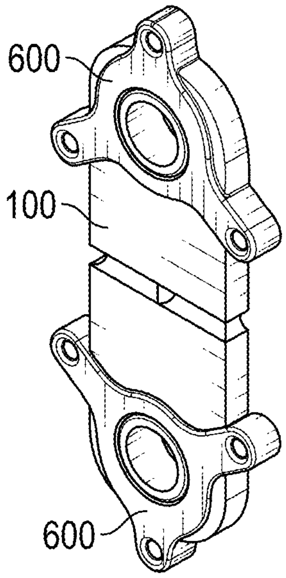
FIG. 19B is a perspective view of the radiostereometric cover and the tether assembly of FIG. 19A.
Figure 19C:
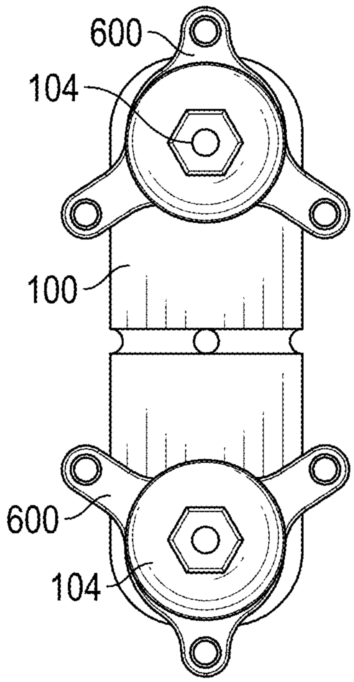
FIG. 19C is a front view of the radiostereometric cover and the tether assembly of FIG. 19A with coupling members according to an embodiment of the present disclosure.
Figure 19D:
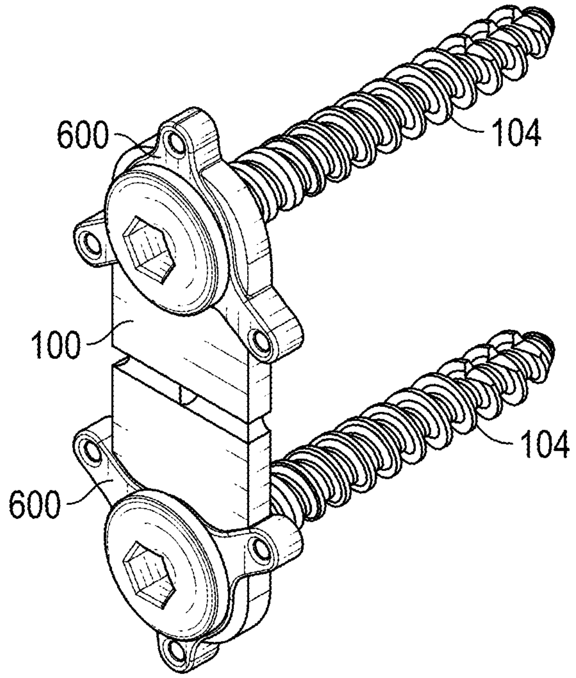
FIG. 19D is a perspective view of the radiostereometric cover, the tether assembly, and the coupling members of FIG. 19C.

FIG. 19A is an exploded perspective view of the radiostereometric cover 600 and a tether assembly 100 according to an embodiment of the present disclosure. FIG. 19B is a perspective view of the radiostereometric cover 600 and the tether assembly 100. FIG. 19C is a front view of the radiostereometric cover 600 and the tether assembly 100 with coupling members 104 according to an embodiment of the present disclosure. FIG. 19D is a perspective view of the radiostereometric cover 600, the tether assembly 100, and the coupling members 104.

The radiostereometric cover 600 may be configured so that with the tether assembly 100 received within the radiostereometric cover 600, and the coupling member 104 received in the radiostereometric cover 600 and the tether assembly 100, the radiostereometric cover 600 is captive on the tether assembly 100. Thereby fixing the location of the cover radiostereometric beads 610 relative to the tether assembly 100.

When the tether assembly 100 is implanted with a first radiostereometric cover 600 received on the first end 110 and a second radiostereometric cover 600 received on the second end 112, the tether assembly 100 may function as previously described for the tether assembly 100' in regards to radiostereometric analysis.

The cover width 606 may be sized so that the coupling members 104 may be in direct contact with the grommets 103 and the grommets 103 may be in direct contact with a surface of a bone, thereby allowing the tether assembly 100 to freely rotate as the bone grows and the angle α increases. Since the tether assembly 100 may be allowed to freely rotate, the rotation of the tether assembly 100 may not exert a rotational force on the coupling members 104, thereby reducing the risk of disengaging the coupling members 104 from the bone.

A method for radiostereometric analysis of a growth plate may include the following steps:

1. Implanting three radiostereometric beads in a triangular pattern in an epiphyseal portion of a bone.
2. Implanting three radiostereometric beads in a triangular pattern in a metaphyseal portion of a bone.
3. Implanting one or more tether assemblies across a physis of a bone, the tether assemblies implanted at an angle corresponding to a desired degree of anteversion correction.
4. Using radiostereometric analysis to monitor the growth of the physis and/or the rotation of the epiphyseal portion relative to the metaphyseal portion.

An alternate method for radiostereometric analysis of a growth plate may include the following steps:

1. Selecting one or more tether assemblies having three radiostereometric beads in a triangular pattern on a first end and three radiostereometric beads in a triangular pattern on a second end.
2. Implanting the one or more tether assemblies across a physis of a bone, the tether assemblies implanted at an angle corresponding to a desired degree of anteversion correction.
3. Securing the first end of each of the one or more tether assemblies to an epiphyseal portion of bone using coupling members and securing the second end of each of the one or more tether assemblies to a metaphyseal portion of bone using coupling members.
4. Using radiostereometric analysis to monitor the growth of the physis and/or the rotation of the epiphyseal portion relative to the metaphyseal portion.

An alternate method for radiostereometric analysis of a growth plate may include the following steps:

1. Selecting one or more tether assemblies and one or more radiostereometric sleeves and/or radiostereometric covers, wherein each of the one or more radiostereometric sleeves and/or radiostereometric covers includes three radiostereometric beads in a triangular pattern.
2. Coupling a first radiostereometric sleeve and/or a first radiostereometric cover to a first end of the tether assembly. Coupling a second radiostereometric sleeve and/or a second radiostereometric cover to a second end of the tether assembly.
3. Implanting the one or more tether assemblies across a physis of a bone, the tether assemblies implanted at an angle corresponding to a desired degree of anteversion correction.
4. Securing the first end each of the one or more tether assemblies to an epiphyseal portion of bone using coupling members and securing the second end of each of the one or more tether assemblies to a metaphyseal portion of bone using coupling members.
5. Using radiostereometric analysis to monitor the growth of the physis and/or the rotation of the epiphyseal portion relative to the metaphyseal portion.

Those of skill in the art will recognize that this is only one of many potential methods that may be used for radiostereometric analysis of a growth plate. In alternative embodiments, different methods may be used for radiostereometric analysis of a growth plate. Further, the methods set forth above may be used for radiostereometric analysis in conjunction with other implants besides the tether assemblies specifically disclosed herein.

Figure 20A:
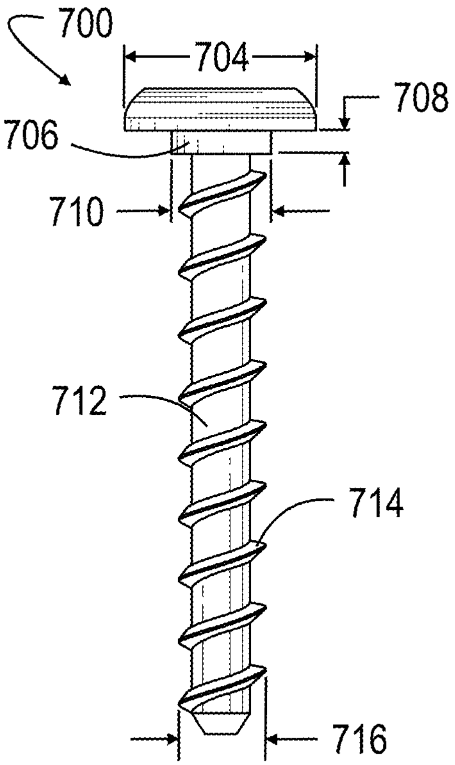
FIG. 20A is a front view of a coupling member according to an embodiment of the present disclosure.
Figure 20B:
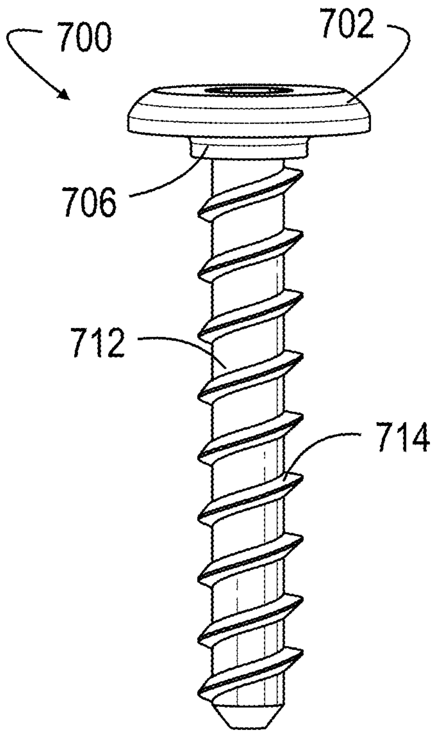
FIG. 20B is a perspective view of the coupling member of FIG. 20A.
Figure 20C:
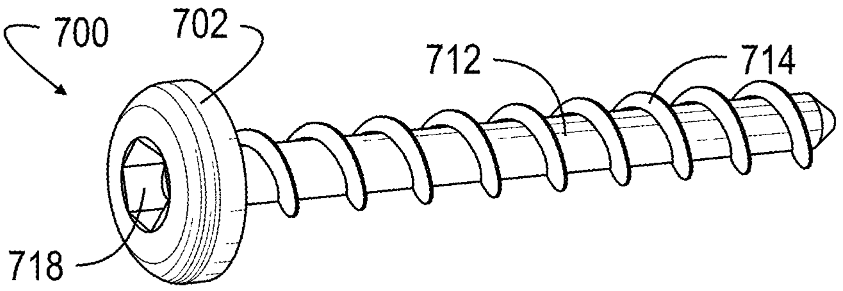
FIG. 20C is a perspective view of the coupling member of FIG. 20A.

FIG. 20A is a front view of a coupling member 700 according to an embodiment of the present disclosure. FIG. 20B is a perspective view of the coupling member 700, and FIG. 20C is a perspective view of the coupling member 700. The coupling member 700 may include similar function and features previously described for the coupling member 104.

The coupling member 700 may be configured to secure a first end and/or a second end of a tether to a portion of a bone. The coupling member 700 may further be configured so that, with a first coupling member 700 securing the first end to a first portion of bone, and a second coupling member 700 securing the second end to a second portion of bone, the first coupling member may be configured to allow the first end to rotate relative to the first portion and the second coupling member may be configured to allow the second end to rotate relative to the second portion. The coupling member 700 may be cannulated to facilitate insertion over a guide wire.

Figure 21:
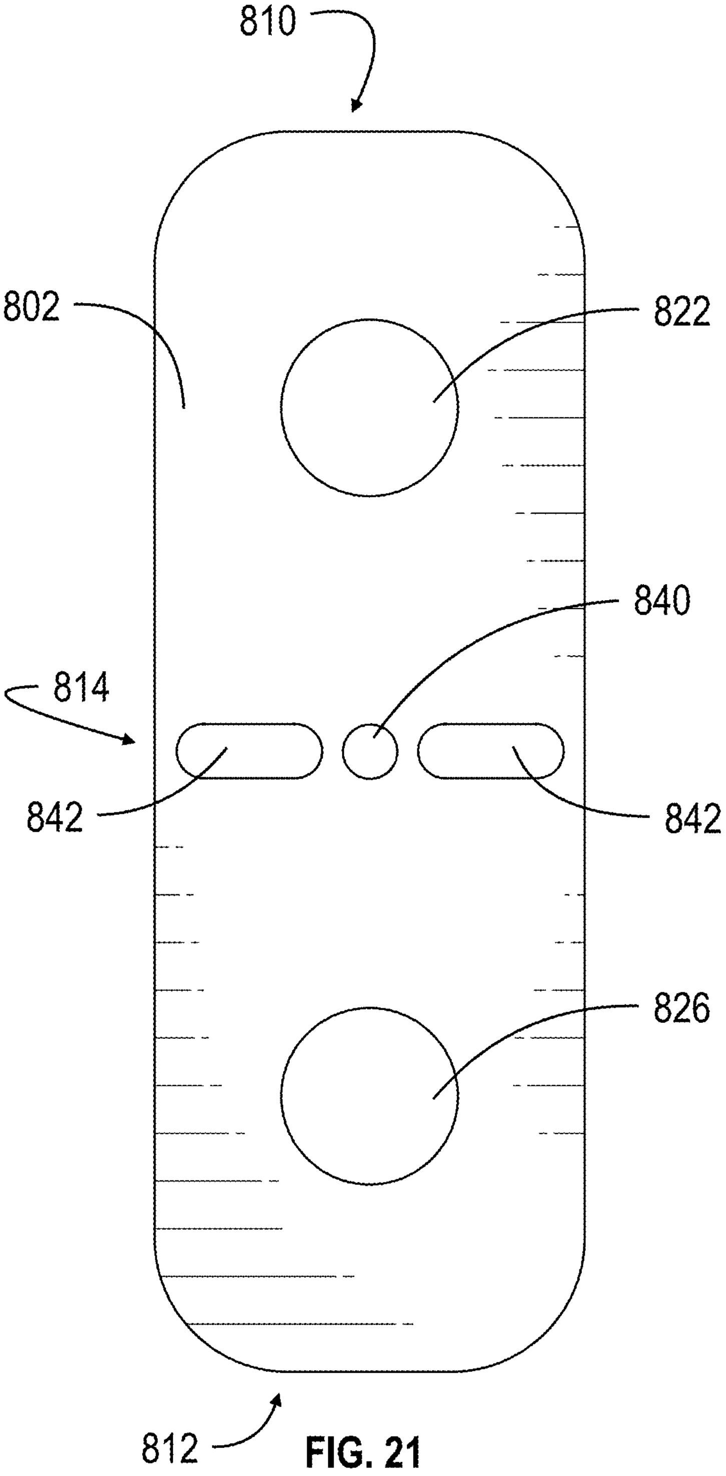
FIG. 21 is a front view of a tether according to an embodiment of the present disclosure.

The coupling member 700 may include a head portion 702 having a head width 704, a shoulder portion 706 having a shoulder height 708 and a shoulder diameter 710, a shank 712, screw threads 714, a thread diameter 716, and a drive feature 718. The coupling member 700 may be configured to be received in a first aperture 822 and/or a second aperture 826 of a tether 802 (as shown in FIG. 21). The head portion 702 may include the drive feature 718. The head width 704 may be larger than the first aperture 822 and/or the second aperture 826 so that the head portion 702 may not pass through the first aperture 822 and/or the second aperture 826.

The drive feature 718 may have a hexalobe geometry or the like. In alternative embodiments, the drive feature 718 may have a different non-circular geometry or may be replaced by one or more positive features such as a boss or any other driver tip geometry known in the art.

The shoulder portion 706 may be configured to be received in the first aperture 822 and/or the second aperture 826. The shoulder diameter 710 may be smaller than a diameter of the first aperture 822 and/or the second aperture 826 so that the tether 802 may freely rotate relative to the coupling member 700. The shoulder height 708 may be greater than a thickness of the tether 802 so that the coupling member may be seated against a surface of the bone. The shoulder height 708 may be configured so that, with the shoulder portion 706 seated against the surface of the bone, the head portion 702 may be spaced apart from the tether, thereby allowing the tether 802 to rotate relative to the coupling member 700.

The screw threads 714 may extend along the shank 712 and may be configured to threadably engage a bone to secure the coupling member 700 to the bone. The thread diameter 716 may be less than the shoulder diameter 710 so that the shoulder portion 706 may be seated against the surface of the bone.

FIG. 21 is a front view of a tether 802 according to an embodiment of the present disclosure. The tether 802 may include similar function and features previously described for the tether 102. The tether 802 may be securable to a bone having a growth plate that separates a first portion of the bone from a second portion of the bone. With the first end 810 secured to the first portion of the bone and the second end 812 secured to the second portion of the bone, the first end 810 and the second end 812 may be configured to apply a rotational force to the first portion relative to the second portion in response to the first end 810 being urged away from the second end 812 as a result of growth of the bone urging the first portion away from the second portion. The first portion of the bone may be an epiphyseal portion 62 and the second portion of the bone may be a metaphyseal portion 64.

A spiral growth tether system may include the tether 802, a first coupling member 700, and a second coupling member 700. The tether 802 may include a first end 810, a second end 812, and a central portion 814 between the first end 810 and the second end 812. The first end 810 may include a first aperture 822 configured to receive the coupling member 700. The second end 812 may include a second aperture 826 configured to receive the coupling member 700.

The tether 802 may be configured so that the first end and the second end may separate at the central portion 814 in response to the first end 810 being urged away from the second end 812 as a result of growth of the bone urging a first portion of the bone away from a second portion of the bone.

The central portion 814 may include a frangible region 815 including a third aperture 840 and one or more central apertures 842 configured to reduce a cross-sectional area of the frangible region 815 such that, in response to the first end 810 being urged away from the second end 812, the frangible region 815 may break at the third aperture 840 and the one or more central apertures 842.

Figure 22:
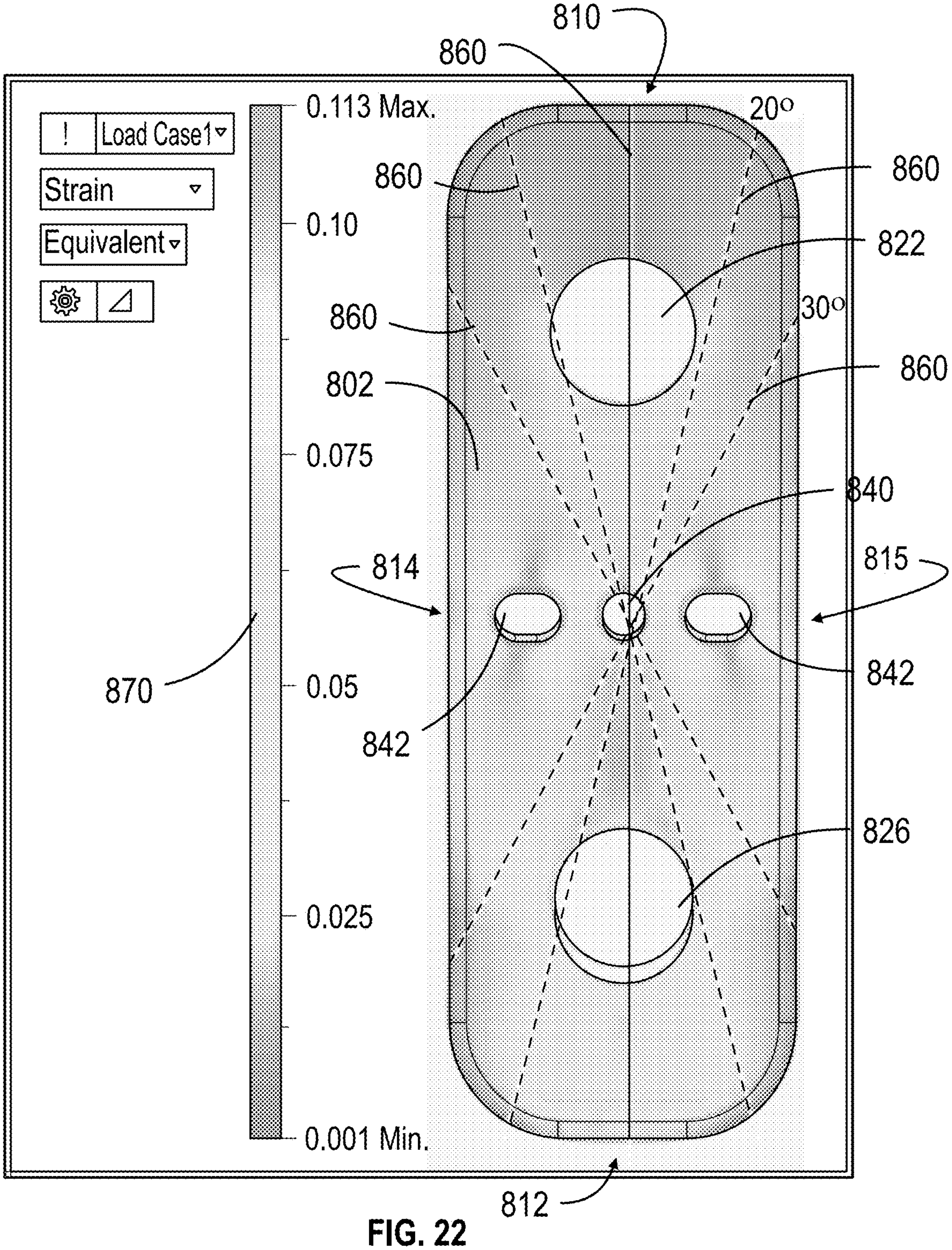
FIG. 22 is a front view of an FEA analysis of the tether of FIG. 21 according to an embodiment of the present disclosure.

FIG. 22 is a front view of an FEA analysis of the tether 802 according to an embodiment of the present disclosure. The size and/or shape of the third aperture 840 and/or the central apertures 842 may be configured so that the first end 810 separates from the second end 812 when, as a result of growth of the bone urging the first portion away from the second portion, a force is applied. In an embodiment, the tether 802 may be configured so that the first end 810 may separate from the second end 812 when the force on the tether 802 resulting from bone growth is between 400 N and 500 N. To achieve separation of the first end 810 and the second end 812 within the desired force range, the size and/or shape of the third aperture 840 and/or the central apertures 842 may be altered. Additionally, or alternatively, to achieve separation of the first end 810 and the second end 812 within the desired force range, the material properties of the tether 802 may be adjusted and/or selected. The tether 802 may include a strap formed of a polymer, such as, polyethylene, nylon, PEEK, urethane, or another implant quality polymer with desired mechanical properties. Additionally, or alternatively, the tether 802 may include a strap formed with other implant quality materials with the desired mechanical properties, such as, stainless steel, titanium, silk, allograft material, etc.

An FEA analysis may be used to evaluate potential materials and/or potential geometries of the tether, including size and/or shape of the first aperture 822, the second aperture 826, the third aperture 840, and/or the central apertures 842. Additionally, or alternatively, an FEA analysis may be used to evaluate potential geometries of the tether, including tether height, tether width, and/or tether thickness. A stress gradient 870 may indicate potential stresses leading to material failure and/or location of a potential material failure. Any or all of the previously mentioned parameters may be adjusted and tested to achieve a tether 802 configured to separate between 400 N and 500 N, whereby the force exerted by a growth plate may be approximately 500 N.

The tether 802 may also include one or more orientation indicators 860. The one or more orientation indicators 860 may be lines on a surface of the tether 802, the orientation indicators 860 may include a line along a longitudinal axis of the tether, or 0 degrees, and lines at +20 degrees from the longitudinal axis, and/or +30 degrees from the longitudinal axis. Additional, and/or alternative, orientation indicators 860 may also be included.

Figure 23:
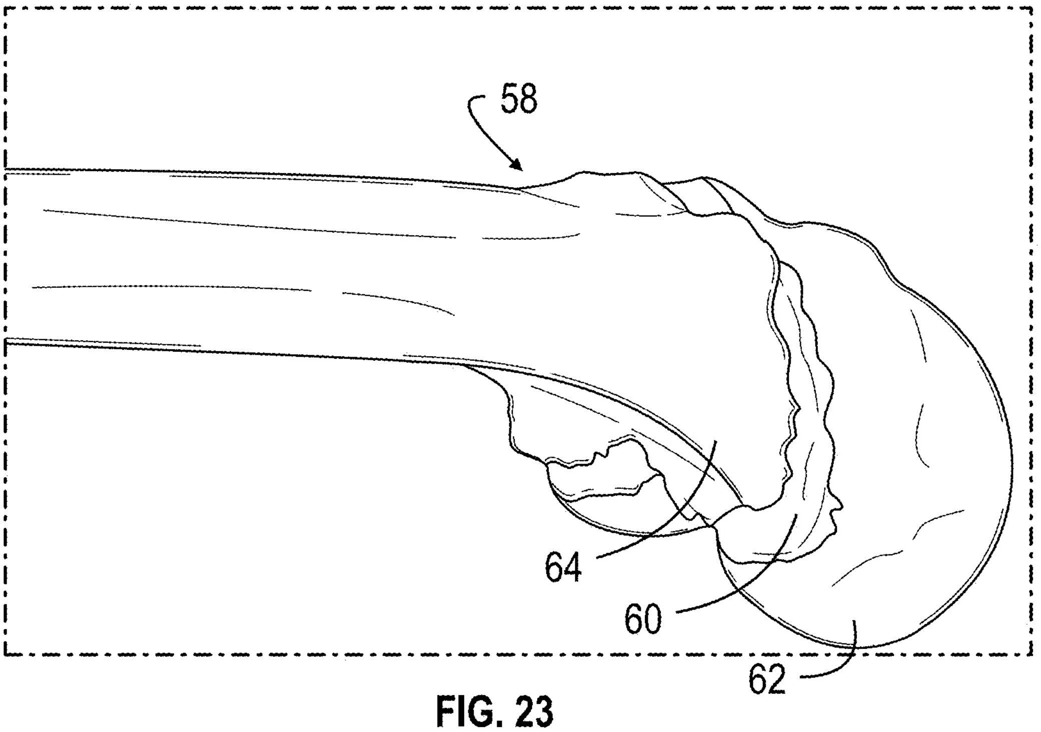
FIG. 23 is a perspective view of an exemplary partial femur.
Figure 24:
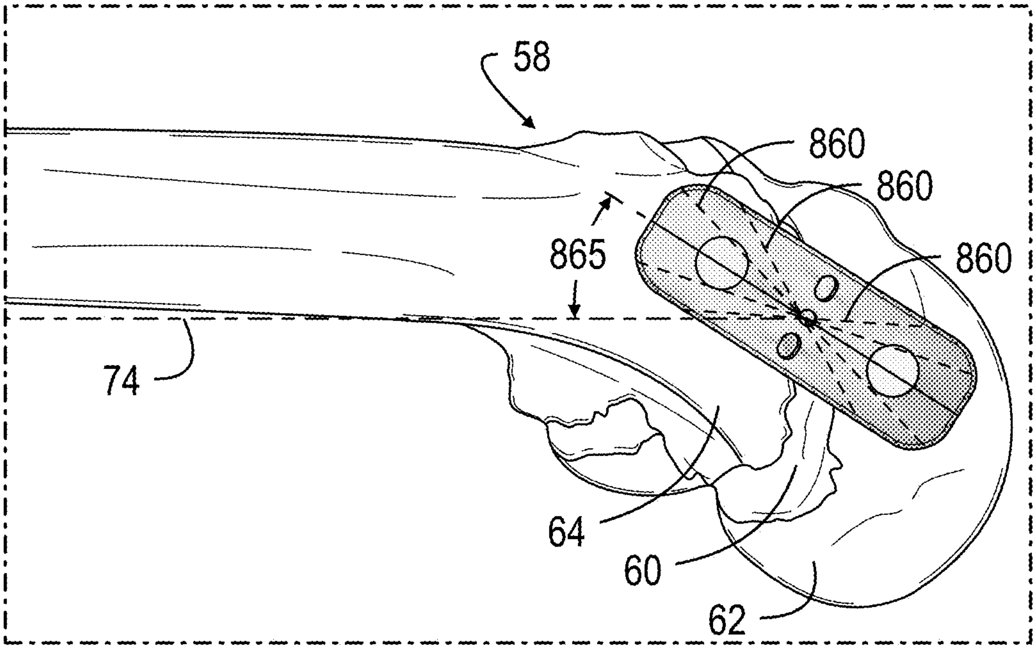
FIG. 24 is a perspective view of the tether of FIG. 21 oriented on the partial femur of FIG. 23 according to an embodiment of the present disclosure.

FIG. 23 is a perspective view of an exemplary partial femur 58. FIG. 24 is a perspective view of the tether 802 oriented on the partial femur 58 according to an embodiment of the present disclosure. The femur 58 may include an epiphyseal portion 62, a metaphyseal portion 64, and a physis 60 (or growth plate) between the epiphyseal portion 62 and the metaphyseal portion 64.

The orientation indicators may be used for aligning the tether 802 at predetermined angles relative to a longitudinal axis 74 of the bone. A surgeon may angle the tether 802 so that the appropriate orientation indicator 860 may be generally parallel to the longitudinal axis 74 of the bone. The tether 802 may then be secured at the desired orientation angle 865 to achieve the desired rotational correction (as shown in FIG. 6).

The foregoing disclosure describes only selected embodiments encompassed within the scope of the disclosure. Those of skill in the art will recognize that the principles taught herein may be applied to generate many alternative concepts. For example, various clips, clasps, staples, plates, screws, and/or other fastening systems may be used to secure two sections of a bone together on either side of a growth plate. Such fastening systems may be made deliberately releasable, through detachable connections and/or breakable components, to effect release when the desired anteversion correction has been obtained.

Reference throughout this specification to “an embodiment” or “the embodiment” means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term “proximal” means a location at the end of a part that faces a user when the user is installing the part. The term “distal” means a location at the opposite end of the proximal end. For example, when a user installs a bone screw into a material with a driver, the end of the bone screw engaged with the driver is the proximal end, and the tip of the bone screw that first engages the material is the distal end. The term “cannulated” means having a central bore extending along a longitudinal axis of a part between a proximal end and a distal end of the part. This may facilitate accurate placement of each screw over a temporary, smooth guide pin.

Recitation of the term “first” with respect to a feature or element does not necessarily imply the existence of a second or additional such feature or element. Elements recited in means-plus-function format are intended to be construed in accordance with 35 U.S.C. § 112 (f). It will be apparent to those having skill in the art that changes may be made to the details of the above-described embodiments without departing from the underlying principles set forth herein.

The phrases “connected to,” “coupled to” and “in communication with” refer to any form of interaction between two or more entities, including mechanical, electrical, magnetic, electromagnetic, fluid, and thermal interaction. Two components may be functionally coupled to each other even though they are not in direct contact with each other. The term “coupled” can include components that are coupled to each other via integral formation, as well as components that are removably and/or non-removably coupled with each other. The term “abutting” refers to items that may be in direct physical contact with each other, although the items may not necessarily be attached together. The phrase “fluid communication” refers to two or more features that are connected such that a fluid within one feature is able to pass into another feature. As defined herein the term “substantially” means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A spiral growth tether system securable to a bone comprising a growth plate that separates a first portion of the bone from a second portion of the bone, the spiral growth tether system comprising:

a tether comprising:
- a first end configured to be secured to the first portion;
- a second end configured to be secured to the second portion; and
- a central portion between the first end and the second end, the central portion comprising:
  - a first slot;
  - a second slot; and
  - an aperture positioned proximate a mid-point of the central portion, between the first slot and the second slot, to facilitate alignment of the central portion with the growth plate;

wherein:
- the first end and the second end are configured to separate at the first slot, the second slot, and the aperture in response to the first end being urged away from the second end as a result of growth of the bone urging the first portion away from the second portion.

2. The spiral growth tether system of claim 1, wherein the central portion comprises a frangible region comprising a groove configured to reduce a cross-sectional area of the frangible region such that, in response to the first end being urged away from the second end, the frangible region breaks at the groove.

3. The spiral growth tether system of claim 1, wherein the tether comprises a strap formed of a polymer.

4. The spiral growth tether system of claim 1, further comprising a first coupling member configured to secure the first end to the first portion and a second coupling member configured to secure the second end to the second portion, wherein:
- the first end and the second end are configured to apply a rotational force to the first portion relative to the second portion in response to the first end being urged away from the second end as a result of growth of the bone urging the first portion away from the second portion;
- with the first end secured to the first portion and the second end secured to the second portion, the first coupling member is configured to allow the first end to rotate relative to the first portion and the second coupling member is configured to allow the second end to rotate relative to the second portion; and
- with the first end secured to the first portion, the second end secured to the second portion, and the first end separated from the second end, the spiral growth tether system is configured to permit growth of the bone.

5. The spiral growth tether system of claim 1, wherein:
- the first end comprising a first plurality of radiopaque beads;
- the second end comprising a second plurality of radiopaque beads; and
- the first plurality of radiopaque beads and the second plurality of radiopaque beads are configured as markers for radiostereometric analysis of the growth plate.

6. The spiral growth tether system of claim 5, wherein the first plurality of radiopaque beads comprises three radiopaque beads configured in a first triangular pattern, and the second plurality of radiopaque beads comprises three radiopaque beads configured in a second triangular pattern.

7. A spiral growth tether system securable to a bone comprising a growth plate that separates a first portion of the bone from a second portion of the bone, the spiral growth tether system comprising:

a first coupling member comprising a first head portion and a first shoulder portion configured to seat against and in direct contact with a first surface on the first portion of the bone;

a second coupling member comprising a second head portion and a second shoulder portion configured to seat against and in direct contact with a second surface on the second portion of the bone; and a tether comprising:

a first end comprising a first aperture configured to receive the first coupling member;

a second end comprising a second aperture configured to receive the second coupling member; and a central portion between the first end and the second end;

wherein:

the first end is configured to be secured to the first portion of the bone via the first coupling member so that the first shoulder portion is seated against the first surface of the bone and the first head portion is spaced apart from the first end;

the second end is configured to be secured to the second portion of the bone via the second coupling member so that the second shoulder portion is seated against the second surface of the bone and the second head portion is spaced apart from the second end; and with the first end secured to the first portion and the second end secured to the second portion, the first coupling member is configured to allow the first end to rotate relative to the first portion and the second coupling member is configured to allow the second end to rotate relative to the second portion.

8. The spiral growth tether system of claim 7, wherein the first end and the second end are configured to separate at the central portion in response to the first end being urged away from the second end as a result of growth of the bone urging the first portion away from the second portion.

9. The spiral growth tether system of claim 8, wherein the central portion comprises a frangible region comprising a groove configured to reduce a cross-sectional area of the frangible region such that, in response to the first end being urged away from the second end, the frangible region breaks at the groove.

10. The spiral growth tether system of claim 8, wherein the central portion comprises a frangible region comprising one or more apertures extending thorough the frangible region, thereby reducing a cross-sectional area of the frangible region such that in response to the first end being urged away from the second end, the frangible region breaks at the one or more apertures.

11. The spiral growth tether system of claim 7, wherein:

the first end and the second end are configured to apply a rotational force to the first portion relative to the second portion in response to the first end being urged away from the second end as a result of growth of the bone urging the first portion away from the second portion; and with the first end secured to the first portion, the second end secured to the second portion, and the first end separated from the second end, the spiral growth tether system is configured to permit growth of the bone.

12. The spiral growth tether system of claim 7, wherein:

the first end comprising a first plurality of radiopaque beads;

the second end comprising a second plurality of radiopaque beads; and the first plurality of radiopaque beads and the second plurality of radiopaque beads are configured as markers for radiostereometric analysis of the growth plate.

13. The spiral growth tether system of claim 12, wherein the first plurality of radiopaque beads comprises three radiopaque beads configured in a first triangular pattern, and the second plurality of radiopaque beads comprises three radiopaque beads configured in a second triangular pattern.

14. The spiral growth tether system of claim 7, wherein:

the first shoulder portion defines a first smooth cylindrical surface configured to be received in the first aperture such that the first aperture is rotatable about the first shoulder portion; and the second shoulder portion defines a second smooth cylindrical surface configured to be received in the second aperture such that the second aperture is rotatable about the second shoulder portion.

15. A spiral growth tether system securable to a bone comprising a growth plate that separates a first portion of the bone from a second portion of the bone, the spiral growth tether system comprising:

a tether comprising:

a first end configured to be secured to the first portion;

a second end configured to be secured to the second portion; and a central portion defining a center of the tether;

wherein:

the tether comprises a strap formed of a polymer;

the tether comprises a plurality of lines radiating outward from the center;

the lines are displaced from each other by predetermined angular increments such that the lines can be aligned with a long axis of the bone to facilitate positioning of the tether at a plurality of predetermined angular offsets from the long axis; and the first end and the second end are configured to separate in response to the first end being urged away from the second end as a result of growth of the bone urging the first portion away from the second portion.

16. The spiral growth tether system of claim 15, the tether further comprises a central portion between the first end and the second end, wherein the central portion comprises a frangible region comprising a groove configured to reduce a cross-sectional area of the frangible region such that, in response to the first end being urged away from the second end, the frangible region breaks at the groove.

17. The spiral growth tether system of claim 15, the tether further comprises a central portion between the first end and the second end, wherein the central portion comprises a frangible region comprising one or more apertures extending thorough the frangible region, thereby reducing a cross-sectional area of the frangible region such that in response to the first end being urged away from the second end, the frangible region breaks at the one or more apertures.

18. The spiral growth tether system of claim 15, wherein:

the first end comprising a first plurality of radiopaque beads;

the second end comprising a second plurality of radiopaque beads; and the first plurality of radiopaque beads and the second plurality of radiopaque beads are configured as markers for radiostereometric analysis of the growth plate.

19. The spiral growth tether system of claim 15, further comprising:

a first coupling member comprising a first shoulder portion, the first coupling member configured to secure the first end to the first portion; and a second coupling member comprising a second shoulder portion, the second coupling member configured to secure the second end to the second portion;

wherein:

with the first coupling member secured to the first portion, the first shoulder portion is configured to seat against and in direct contact with a first surface of the bone;

with the second coupling member secured to the second portion, the second shoulder portion is configured to seat against and in direct contact with a second surface of the bone; and with the first end secured to the first portion and the second end secured to the second portion, the first coupling member is configured to allow the first end to rotate relative to the first portion and the second coupling member is configured to allow the second end to rotate relative to the second portion.

20. The spiral growth tether system of claim 15, wherein, with the first end secured to the first portion, the second end secured to the second portion, and the first end separated from the second end, the spiral growth tether system is configured to permit growth of the bone.

* * * * *